United States Patent
Yanagawa et al.

(10) Patent No.: US 11,002,728 B2
(45) Date of Patent: May 11, 2021

(54) METHOD FOR EVALUATING ACTIVITY OF G PROTEIN-COUPLED RECEPTOR (GPCR)

(71) Applicant: RIKEN, Saitama (JP)

(72) Inventors: Masataka Yanagawa, Saitama (JP); Yasushi Sako, Saitama (JP); Michio Hiroshima, Saitama (JP); Masato Yasui, Saitama (JP); Masahiro Ueda, Saitama (JP); Yuichi Togashi, Hiroshima (JP)

(73) Assignee: RIKEN, Saitama (JP)

( * ) Notice: Subject to any disclaimer, the term of this patent is extended or adjusted under 35 U.S.C. 154(b) by 280 days.

(21) Appl. No.: 15/957,406

(22) Filed: Apr. 19, 2018

(65) Prior Publication Data
US 2018/0306779 A1 Oct. 25, 2018

(30) Foreign Application Priority Data
Apr. 21, 2017 (JP) .............................. JP2017-084803

(51) Int. Cl.
| G01N 33/53 | (2006.01) |
| G01N 33/50 | (2006.01) |
| G01N 33/74 | (2006.01) |

(52) U.S. Cl.
CPC ......... *G01N 33/5026* (2013.01); *G01N 33/74* (2013.01); *G01N 2333/726* (2013.01); *G01N 2500/10* (2013.01)

(58) Field of Classification Search
None
See application file for complete search history.

(56) References Cited

PUBLICATIONS

Tang, X.L. et al., "Orphan G protein-coupled receptors (GPCRs): biological functions and potential drug targets", Acta Pharmacologica Sinica, vol. 33, 2012 (pp. 363-371).
Santos, R. et al., "A comprehensive map of molecular drug targets", Nature Reviews/Drug Discovery, vol. 16, 2017 (pp. 19-34).
Zhang, R. et al., "Tools for GPCR drug discovery", Acta Pharmacologica Sinica, vol. 33, 2012 (pp. 372-384).
Hemstapat, K. et al., "A Novel Family of Potent Negative Allosteric Modulators of Group II Metabotropic Glutamate Receptors", The Journal of Pharmacology and Experimental Therapeutics, vol. 322, No. 1, 2007 (pp. 254-264).
DiRaddo, J. O., et al., "Chloride is an Agonist of Group II and III Metabotropic Glutamate Receptors", Molecular Pharmacology, vol. 88, 2015 (pp. 450-459).
Tora, A. S. et al., "Allosteric modulation of metabotropic glutamate receptors by chloride ions", The FASEB Journal, vol. 29, 2015 (pp. 4174-4188).
Neubig, R. R. et al., "International Union of Pharmacology Committee on Receptor Nomenclature and Drug Classification. XXXVIII. Update on Terms and Symbols in Quantitative Pharmacology", Pharmacological Reviews, vol. 55, No. 4, 2003 (pp. 597-606).
Persson, F. et al., "Extracting intracellular diffusive states and transition rates form single-molecule tracking data", Nature Methods, vol. 10, No. 3, 2013 (pp. 265-269).
Okamoto, K. et al., "Variational Bayes Analysis of a Photon-Based Hidden Markov Model for Single-Molecule FRET Trajectories", Biophysical Journal, vol. 103, 2012 (pp. 1315-1324).
Calebiro, D. et al., "Single-molecule analysis of fluorescently labeled G-protein-coupled receptors reveals complexes with distinct dynamics and organization", PNAS, vol. 110, No. 2, 2013 (pp. 743-748).
Mangmool, S. et al., "G(i/o) Protein-Dependent and -Independent Actions of Pertussis Toxin (PTX)", Toxins (Basel), vol. 3, 2011 (pp. 884-899).
Nobles, M. et al., "Heterotrimetric G proteins precouple with G protein-coupled receptors in living cells", PNAS, vol. 102, No. 51, 2005 (pp. 18706-18711).
Gales, C. et al., "Probing the activation-promoted structural rearrangements in preassembled receptor-G protein complexes", Nature Structural and Molecular Biology, vol. 13, No. 9, 2006 (pp. 778-786).
Qin, K. et al., "Inactive-state preassembly of G(q)-coupled receptors and G(q) heterotrimers", Nat Chem Biol., vol. 7, No. 10, 2011 (pp. 740-747).
Kusumi, A. et al., "Cell surface organization by the membrane skeleton", Current Opinion in Cell Biology vol. 8, 1996 (pp. 566-574).
Hern, J. A. et al., "Formation and dissociation of M1 muscarinic receptor dimers seen by total internal reflection fluorescence imaging of single molecules", PNAS, vol. 107, No. 6, 2010 (pp. 2693-2698).
De Lean, A. et al., "A Ternary Complex Model Explains the Agonist-specific Binding Properties of the Adenylate Cyclase-coupled beta-adrenergic Receptor", The Journal of Biological Chemistry, vol. 255, No. 15, 1980 (pp. 7108-7117).
Drake, M. T. et al., "Trafficking of G Protein-Coupled Receptors", Circulation Research, vol. 99, 2006 (pp. 570-582).
Puthenveedu, M. A. et al., "Cargo Regulates Clathrin-Coated Pit Dynamics", Cell, vol. 127, 2006 (pp. 113-124).
Henry, A. G. et al., "Regulation of Endocytic Clathrin Dynamics by Cargo Ubiquitination", Developmental Cell, vol. 23, 2012 (pp. 519-532).
Niwa, H. et al., "Efficient selection for high-expression transfectants with a novel eukaryotic vector", Gene, vol. 108, 1991 (pp. 193-199).
Gaidarov, I. et al., "Spatial control of coated-pit dynamics in living cells", Nature Cell Biology, vol. 1, 1999 (pp. 1-7).
Tanaka, K.A.K. et al., "Membrane molecules mobile even after chemical fixation", Nature Methods, vol. 7, No. 11, 2010 (pp. 865-866).

(Continued)

*Primary Examiner* — Michael D Pak
(74) *Attorney, Agent, or Firm* — Lucas & Mercanti, LLP

(57) ABSTRACT

It is an object to provide a method for evaluating a medicinal substance targeting a G protein-coupled receptor (GPCR). Specifically, the present invention relates to a method for evaluating the activity of a GPCR comprising a step of bringing a target substance into contact with a cell expressing a GPCR on the cell membrane; and a step of determining the diffusive dynamics of the GPCR on the cell membrane.

1 Claim, 11 Drawing Sheets

(56) References Cited

PUBLICATIONS

Bronson, J.E. et al., "Learning Rates and States from Biophysical Time Series: A Bayesian Approach to Model Selection and Single-Molecule FRET Data", Biophysical Journal, vol. 97, 2009 (pp. 3196-3205).

Kusumi, A. et al., "Confined Lateral Diffusion of Membrane Receptors as Studied by Single Particle Tracking (Nanovid Microscopy). Effects of Calcium-Induced Differentiation in Cultured Epithelial Cells", Biophysical Journal, vol. 65, 1993 (pp. 2021-2040).

Xiao, Z. et al., "Single-Molecule Study of Lateral Mobility of Epidermal Growth Factor Receptor 2/HER2 on Activation", J. Phys. Chem. B., vol. 112, 2008 (pp. 4140-4145).

Wilson, K. M. et al., "Single particle tracking of cell-surface HLA-DR molecules using R-phycoerythrin labeled monoclonal antibodies and fluorescence digital imaging", Journal of Cell Science, vol. 109 (part 8), 1996 (pp. 2101-2109).

Yanagawa, M. et al., "Glutamate Acts as a Partial Inverse Agonist to Metabotropic Glutamate Receptor with a Single Amino Acid Mutation in the Transmembrane Domain", The Journal of Biological Chemistry, vol. 288, No. 14, 2013 (pp. 9593-9601).

Yanagawa, M. et al., "Activation Switch in the Transmembrane Domain of Metabotropic Glutamate Receptor", Molecular Pharmacology, vol. 76, 2009 (pp. 201-207).

Fredriksson, R. et al., "The G-Protein-Coupled Receptors in the Human Genome Form Five Main Families. Phylogenetic Analysis, Paralogon Groups, and Fingerprints", Molecular Pharmacology, vol. 63, No. 6, 2003 (pp. 1256-1272).

Munk, C. et al., "GPCRdb: the G protein-coupled receptor database—an introduction", British Journal of Pharmacology, vol. 173, 2016 (pp. 2195-2207).

Printout of webpage for the 54th Annual Meeting of the Biophysical Society of Japan (BSJ54). https://www.aeplan.co.jpbsj2016enindex.html. Including both English and Japanese versions of the web page. 2016 (total 4 pages).

The Biophysical Society of Japan, "Abstract entitled Comparative analysis of diffusion relationship of G protein-coupled receptors on the living cell surface" (1Pos104), Booklet of the 54th Annual Meeting of the Biophysical Society of Japan, Supplement 1-2, vol. 56, 2016 (4 pages).

Yanagawa, M. et al., "Comparative analysis of diffusion-function relationship of G protein-coupled receptors on the living cell surface", RIKEN, Poster (1 page total).

a b c d

METHOD FOR EVALUATING ACTIVITY OF G PROTEIN-COUPLED RECEPTOR (GPCR)

CROSS-REFERENCE FOR RELATED APPLICATION

The present application claims priority from Japanese patent application JP 2017-084803 filed on Apr. 21, 2017, the contents of which are hereby incorporated by reference into this application.

BACKGROUND OF THE INVENTION

Field of the Invention

The present invention relates to a method for evaluating the activity of a G protein-coupled receptor (hereinafter, referred to as "GPCR").

Background Art

The GPCR is a generic name for membrane proteins that occupy an important position as a drug discovery target. At present, although 33% of small molecule drugs target some kind of GPCR and form a market of 20 trillion yen annually, the receptors as the targets are only 6% of the about 800 human GPCRs (Tang, X. L., Wang, Y., Li, D. L., Luo, J. & Liu, M. Y. Orphan G protein-coupled receptors (GPCRs): biological functions and potential drug targets. Acta Pharmacol Sin 33, 363-71, 2012; and Santos, R. et al. A comprehensive map of molecular drug targets. Nat Rev Drug Discov 16, 19-34, 2017)[1,2]. In particular, among 300 GPCRs having high potentiality as drug discovery targets, about 100 GPCRs are orphan receptors of which the physiological ligands are unknown. If the ligand of an orphan GPCR can be efficiently identified, it will lead to creation of first-in-class compounds for each orphan GPCR.

Conventionally, evaluation of a medicinal effect on a GPCR as a target at a level of cultured cells has been performed using downstream cell response of the GPCR, such as an increase or decrease of $Ca^{2+}$ or cAMP, as an index (Zhang, R. & Xie, X. Tools for GPCR drug discovery. Acta Pharmacol Sin 33, 372-84, 2012)[3]. However, in almost all of orphan GPCRs, the downstream signaling pathway is unknown, and it is impossible to tell an index that can be used for evaluating a medicinal effect.

SUMMARY OF THE INVENTION

The present invention has been made in view of the circumstances described above, and an object of the invention is to provide a method for efficiently evaluating a medicinal substance using a GPCR as a target.

As a result of diligent studies for solving the above-described problems, it was found that medicinal effects on various GPCRs can be evaluated by quantifying the diffusive dynamics of GPCR molecules through application of a technique of imaging molecules on a living cell surface at a single-molecule level, and the present invention was accomplished.

That is, the present invention encompasses the followings:

(1) A method for evaluating activity of a GPCR comprising bringing a target substance into contact with a cell expressing a GPCR on a cell membrane; and determining diffusive dynamics of the GPCR on the cell membrane;

(2) The method according to aspect (1), wherein the GPCR includes a fluorescent label on a C-terminus;

(3) The method according to aspect (1) or (2), wherein the diffusive dynamics is determined as a mean square displacement or an average diffusion coefficient; and (4) The method according to any one of aspects (1) to (3), wherein slow diffusive dynamics compared to that of a negative control indicates that the target substance is a GPCR agonist, or fast diffusive dynamics compared to that of a negative control indicates that the target substance is a GPCR inverse agonist.

According to the present invention, a medicinal substance targeting a GPCR can be efficiently identified.

The present description includes part or all of the contents as disclosed in Japanese Patent Application No. 2017-084803, which is a priority document of the present application.

DETAILED DESCRIPTION OF THE PREFERRED EMBODIMENTS

Figure 1:
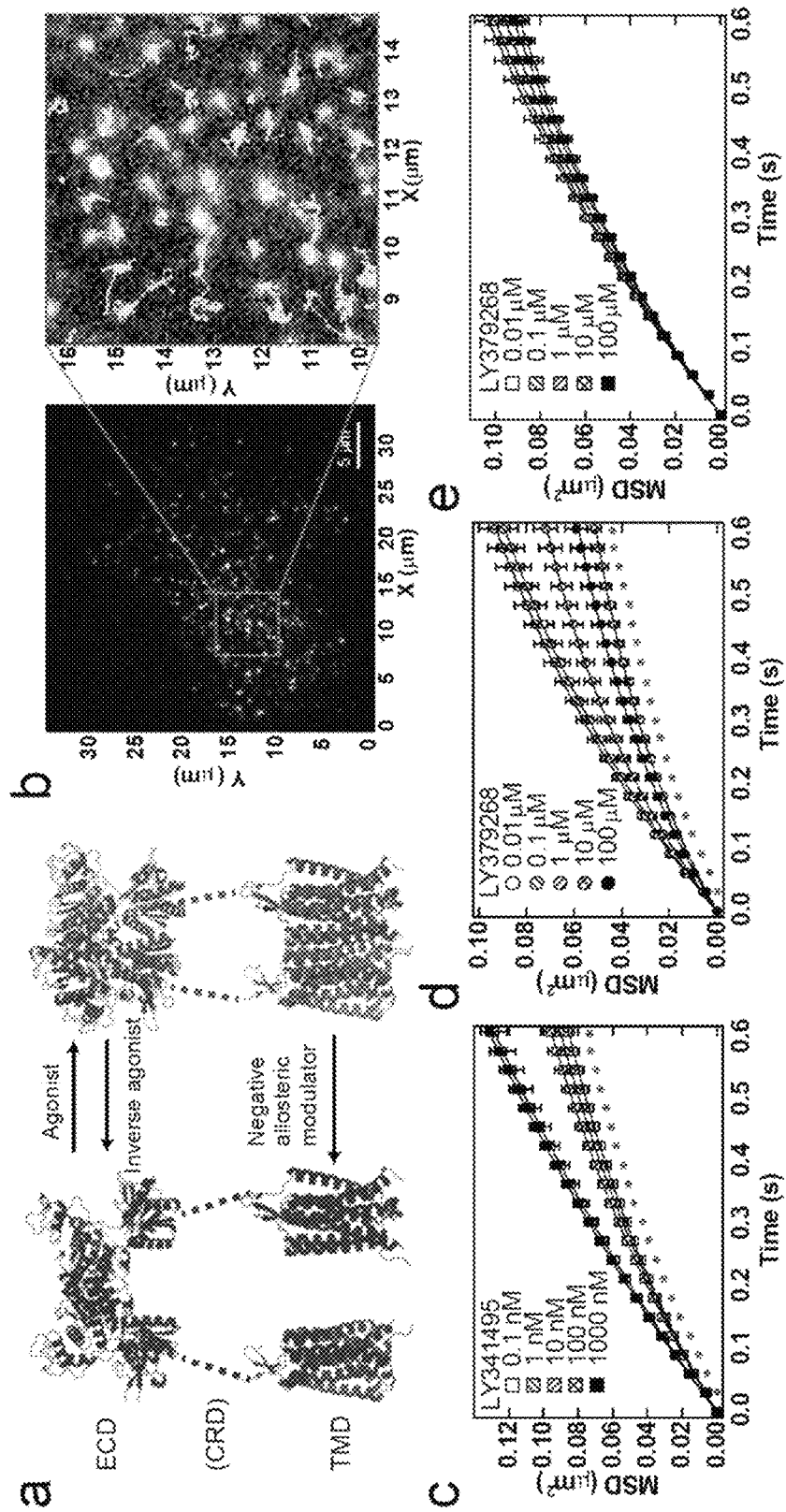
FIG. 1 shows an activation model, a single-molecule fluorescence image, and MSD-Δt plots of mGluR. (a) Activation model of mGluR: X-ray crystal structures (inactive state (blue): 1EWT, active state (red): 1EWK) of ECD of mGluR1 were drawn with PyMol (http://www.pymol.org/). The transmembrane domain (TMD) in both states was drawn with 4OR2. (b) Example of total internal reflection fluorescence microscopy image of TMR-labeled mGluR3 (left: overall image of cells, right: enlarged view of the portion surrounded by the dotted line in the left panel): The tracks of mGluR3 as the result of single molecule tracking (SMT) analysis are shown in yellow in the right panel. (c to e) MSD-Δt plots of the tracks of mGluR3 under a variety of ligand conditions: An inverse agonist (LY341495) concentration-dependent change is shown in (c). An agonist (LY379268)-dependent change in the presence of 100 nM LY314195 is shown in (d). Plots in the presence of 1 μM MNI137 in addition to the ligand condition in (d) are shown in (e). All data are shown as mean±standard error (n=20 cells). *: A significant change in MSD at each Δt between five ligand concentration conditions (p<0.01: one-way ANOVA).

The present invention will now be described in detail.

The method for evaluating the activity of a GPCR according to the present invention (hereinafter, referred to as "the method") includes a step of bringing a target substance into contact with a cell expressing a GPCR on the cell membrane; and a step of determining the diffusive dynamics of the GPCR on the cell membrane. The present invention is based on the finding that the active state of a GPCR correlates with the diffusive dynamics of the GPCR on a cell membrane. In the method, since the movement of the GPCR itself is used as an index, even if the GPCR is an unknown downstream orphan GPCR, the medicinal effect can be evaluated. In addition, the method can identify a prophylactic or therapeutic agent for a disease associated with each GPCR. The present invention can be used for screening candidate substances for a medicinal substance targeting a GPCR.

In the present specification, the term "G protein-coupled receptor" (also referred to as "GPCR") refers to a receptor coupling with G protein and transmitting a signal from the outside into a cell. GPCRs have a common structure passing through the cell membrane seven times and constitute GPCR superfamily. The GPCRs are classified into six classes A to F based on the similarity of amino acid sequences and functions. The GPCRs are derived, for example, from a mammal, preferably a primate, and more preferably a human.

The GPCR may be any GPCR belonging to the GPCR superfamily. For example, evolutionarily diverse GPCRs far away from each other in the phylogenetic tree, as the GPCRs shown in Table 1, can be used as targets. In addition, since G protein may have any coupling specificity, the medicinal effects regarding GPCRs, such as F2R, driving multiple signaling systems also can be evaluated with a single index.

In the method, a cell expressing a GPCR on the cell membrane is prepared. The cell may be any cell that can express the GPCR on the cell membrane and is, for example, from a eukaryote, preferably from a vertebrate, more preferably from a mammal, further preferably from a primate, and most preferably from a human. A cell not expressing the GPCR to be expressed and expressing G protein to be coupled with the GPCR is preferably used. Examples of the cell include human-derived cell lines, such as a HEK293 cell, and primary cultured cells. The GPCR preferably includes a fluorescent label for single-molecule imaging. Although the fluorescent label can be attached to any position of the GPCR, the label is preferably attached to the C-terminus. As the fluorescent label, for example, a fluorescent protein, such as mEGFP, can be used. Alternatively, a fluorescent ligand may be covalently bonded by means of attachment of a tag sequence (e.g., HaloTag, SNAP-tag, CLIP-tag). When a tag sequence covalently bonded to a fluorescent protein or fluorescent ligand is used as a fluorescent label, a fusion protein including the GPCR and the fluorescent protein or tag sequence is expressed in the direction from the N-terminus to the C-terminus on the cell membrane. When the C-terminus is labeled with a fluorescent label, the fluorescent protein or tag sequence in the expressed fusion protein is present inside the cell membrane.

For example, a cell is transfected with a gene encoding a fusion protein including a GPCR and a fluorescent protein or tag sequence or an expression vector including the gene by a usual method, and the fusion protein is expressed on the cell membrane. Herein, if the expression level is excessive, only a part of the expressed labeled GPCR is involved in signaling, and the other does not respond in the contact with the target substance. As a result, it is difficult to precisely observe the diffusive dynamics. Accordingly, a low expression level is preferred. For example, a preferred expression level is not greater than several nanomoles in a cell. The expression level is adjusted by the amount of the expression vector to be added at the time of transfection and the promoter strength of the expression vector. As the low expression vector, for example, a CMV promoter-modified vector, such as pFC15 vector (Promega Corporation), can be used.

Subsequently, a target substance is brought into contact with the cell expressing a GPCR on the cell membrane. The target substance to be examined for the effect on the activity of the GPCR by the contact may be any substance, and examples thereof include nucleic acids, peptides, proteins, synthetic compounds, culture supernatants of microorganisms, natural components derived from plants, plant extracts, and animal tissue extracts. The contact means a state in which a target substance can influence GPCR activity, preferably a state in which a target substance can bind to the GPCR. For example, a target substance may be merely added to a medium for GPCR-expressing cells. Alternatively, a target substance may be added to a medium for GPCR-expressing cells together with a certain carrier (e.g., a protein or lipid). A target substance may be directly introduced into a GPCR-expressing cell by microinjection, for example.

Subsequently, the diffusive dynamics (diffusive movement) of the GPCR on the cell membrane is determined. Preferably, the diffusive dynamics is determined using the fluorescent label attached to the GPCR as an index. When HaloTag is used as the fluorescent label, staining with, for example, HaloTag TMR ligand (Promega Corporation) or STELLA Fluo 650 HaloTag ligand (Goryo Chemical, Inc.) is performed. Although the diffusive dynamics of the GPCR can be determined by any known method, for the purpose of the present invention, it is necessary to track the diffusive dynamics of the GPCR at a single molecule level. Accordingly, a method allowing single-molecule imaging is employed. Specifically, under a fluorescence microscope, the fluorescent label attached to the GPCR on the cell membrane of the cells after contact with a target substance is excited with total internal reflection illumination for single-molecule imaging. Subsequently, the diffusive dynamics of the GPCR is determined from the captured fluorescence image. Specifically, information on the bright spot positions and intensities of GPCR molecules is obtained from the captured fluorescence image using bright spot detection algorithm, such as a two-dimensional Gaussian function fitting method. Furthermore, information on the track of each bright spot is obtained from time series images by, for example, connecting bright spots located closest to each other under a certain threshold. Furthermore, the mean square displacement (MSD) or average diffusion coefficient ($D_{Av}$) of the tracks of GPCR molecules in each cell is calculated by the Expression shown in the paragraph "3-4. Image analysis of single-molecule imaging" in the following Examples to show the diffusive dynamics Slow diffusive dynamics of a GPCR on a cell membrane means the active state of the GPCR. In contrast, fast diffusive dynamics of a GPCR means the inactive state of the GPCR. Accordingly, it can be judged that slow diffusive dynamics (MSD or $D_{Av}$) of a GPCR on a membrane cell compared to a negative control (e.g., a cell not brought into contact with the target substance or a cell brought into contact with a vehicle) indicates that the target substance is a GPCR agonist and that fast diffusive dynamics of a GPCR on a cell membrane compared to the negative control indicates that the target substance is a GPCR inverse agonist. The difference of the average diffusion coefficient from that of the control is expected to be about 10% to 50% and is preferably judged based on statistical significance. For this purpose, it is preferred to obtain the results from a larger number of cells. In contrast, when many target substances are evaluated, it is favorable to collect a smaller volume of data. For example, diffusive dynamics of a GPCR is investigated for 10 to 100 cells, preferably 15 to 50 cells, and more preferably 20 to 30 cells. A significant difference of p<0.05, more preferably p<0.01, is routinely used in the t test as criteria for determination of the difference between the mean values of the diffusion coefficients in two groups.

EXAMPLES

Although the present invention will now be described in more detail using Examples, the technical scope of the present invention is not limited to the following Examples.
1. Results
1-1. Relationship Among Average Diffusion Coefficient, Ligand Affinity, and G Protein Activation Ability of mGluR3

Figure 2:
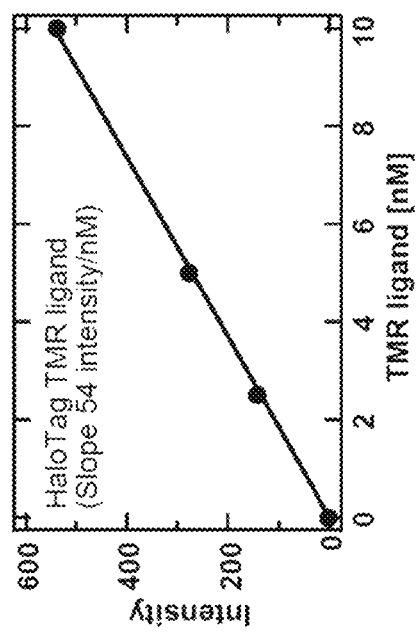
FIG. 2 shows a saturation binding experiment of a TMR ligand to HaloTag-fused mGluR3. (a) Fluorescence spectra of HaloTag TMR ligand at different concentrations. (b) Regression line for concentration estimation of TMR based on the intensities of the fluorescence spectra at 584 nm shown in (a). (c) Specific binding of TMR ligand to HaloTag-fused mGluR3 and non-specific binding to cell membrane estimated from the TMR concentration in solubilized cell supernatant. The concentration of TMR ligand bound to a cell membrane was estimated from the regression line in (b). In the single molecule imaging, 300 nM TMR ligand was used (vertical dotted line). It was estimated from the regression curve ($EC_{50}$: 63 nM, Hill coefficient: 1.9) that about 95% of mGluR3 was labeled under the same conditions as above. (d) Validation of non-specific binding of TMR ligand to HEK293 cell or cover glass in total internal reflection fluorescence microscopy images. The images were obtained by the same treatment as in FIG. 1(b).
Figure 2:
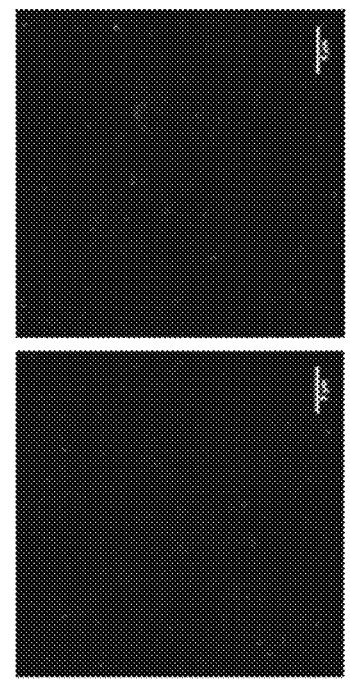
Figure 2:
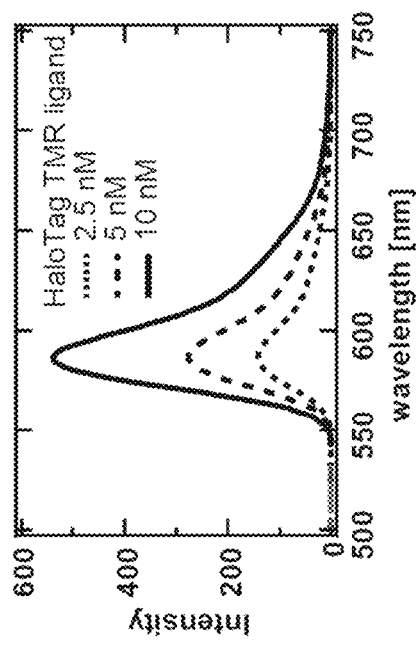
Figure 2:
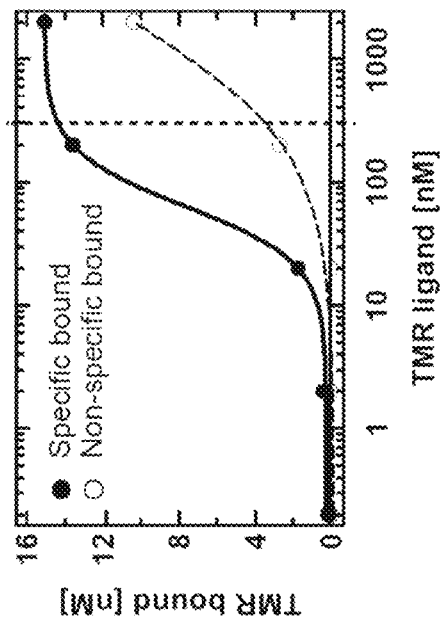
Figure 3:
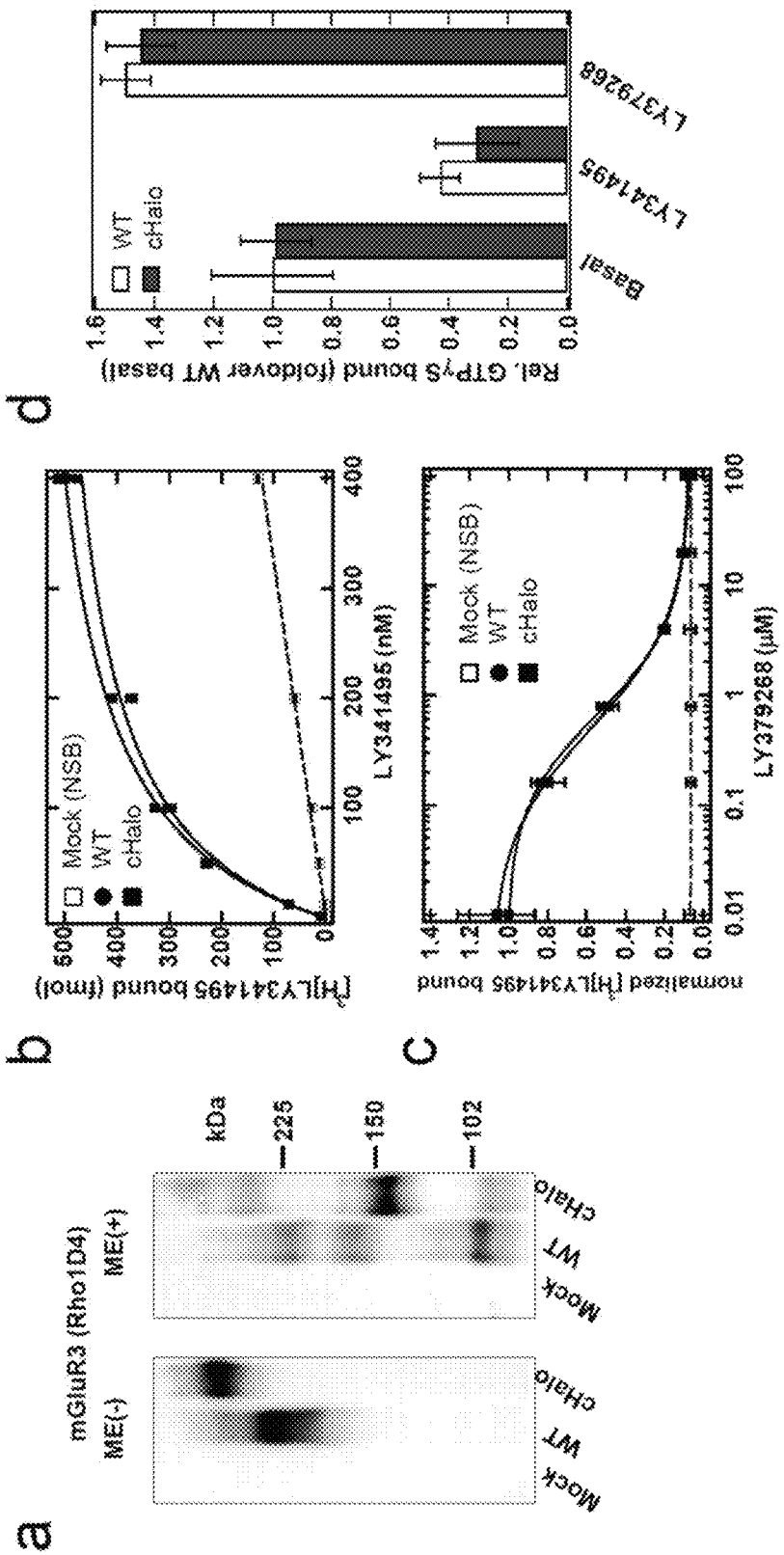
FIG. 3 shows evaluation of influence of HaloTag fusion on the function of mGluR3. (a) Western blotting analysis of cell membrane fractions expressing HaloTag-fused mGluR3 (cHalo) on the C-terminus and wild-type mGluR3 (WT). In solubilization with mercaptoethanol (ME)-free SDS sample buffer, bands of dimers are observed (left panel). In solubilization with ME-containing SDS sample buffer, the disulfide bond crosslinking between ECDs of mGluR3 is reduced, and bands of monomers are detected (right panel). (b and c) Comparison of ligand-binding affinities of mGluR3 fused or not fused with HaloTag. In both the saturation binding experiment (b) of [$^3$H]-LY341495 and the competitive inhibition experiment (c) of [$^3$H]-LY341495 and LY379268, there was no significant difference due to the presence or absence of HaloTag. (d) Comparison of G protein activation abilities of mGluR3 fused or not fused with HaloTag. No significant difference was observed between WT and cHalo in either the absence of a ligand or the presence of 1 μM LY341495 or 100 μM LY379268. The data in (b-d) are shown as mean±standard error (n=3).

In this Example, the relationship between the diffusion coefficient and the activity of a GPCR on a living cell membrane was verified using a metabotropic glutamate receptor (mGluR3) as a model. The mGluR is a member of Class C GPCR, has a large extracellular ligand binding domain (ECD) on the N-terminus, and constantly forms a dimer to function (FIG. 1(a)). The mGluR3 fused with HaloTag at the C-terminus was expressed in HEK293 cells, and movement of bright spots of fluorescent labeled mGluR3 molecules on a living cell membrane was measured with a total internal reflection fluorescence microscope (FIG. 1(b)). It was estimated that under this experimental condition, about 95% of the HaloTag-fused mGluR3 was labeled with tetramethylrhodamine (TMR) (FIG. 2). Incidentally, it was already biochemically confirmed that the fusion of HaloTag to the mGluR3 does not influence the dimerization, ligand-binding affinity, and G protein activation ability (FIG. 3).

Similar single-molecule imaging was performed for 20 cells under various ligand conditions, and the bright spot of each receptor molecule was tracked. Furthermore, a "mean square displacement-time interval plot (MSD-Δt plot)" was formed from the track of each receptor molecule, and the change in the mean value of diffusion range of the ligand concentration-dependent receptor was analyzed (FIG. 1(c to e)). As a result, the MSD of mGluR3 increased depending on the concentration of inverse agonist LY341495 (FIG. 1(c)) and decreased depending on the concentration of agonist LY379268. Furthermore, in the presence of a negative allosteric ligand MNI137[4], the LY379268-dependent decrease of the MSD was suppressed (FIG. 1(e)).

Figure 4:
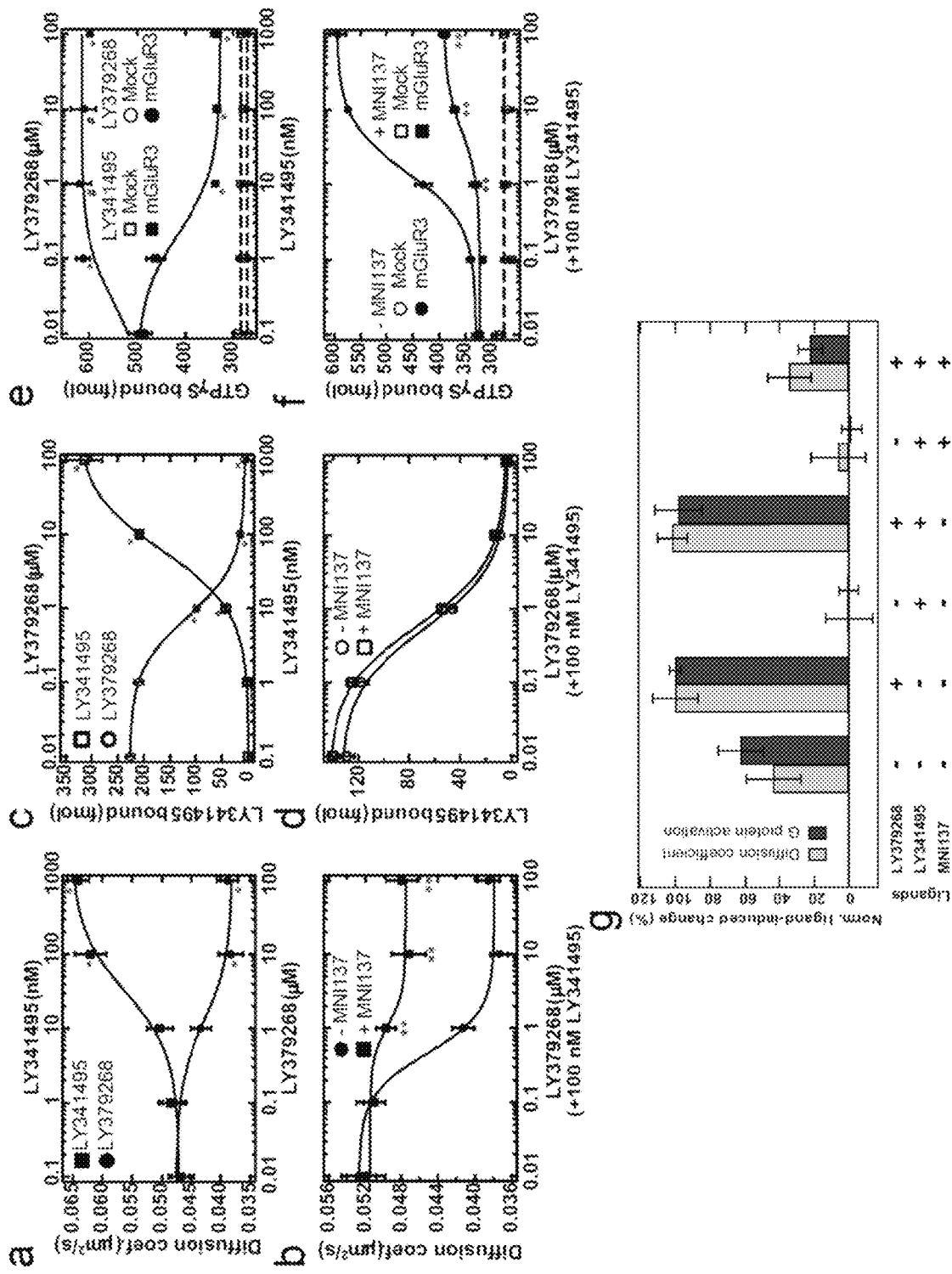
FIG. 4 shows comparison of diffusion coefficient, ligand-binding affinity, and G protein activation ability of mGluR3. (a and b) Ligand concentration-dependent change of $D_{Av}$: LY341495 (■) or LY379268 (●) concentration-dependent changes in the absence of other ligands are shown in (a). LY379268 concentration dependency in the presence of 100 nM LY341495 and the absence of MNI137 (●) or in the presence of 100 nM LY341495 and 1 μM MNI137 (■) is shown in (b). All data are shown as mean±standard error (n=20 cells). *: A point where a significant difference with respect to the leftmost point is observed in each curve in (a) (p<0.01; t-test, two-tailed). **: A point where a significant difference is observed between two curves (in the presence or absence of 1 μM MNI137) in (b) (p<0.01; t-test, two-tailed). (c and d) Ligand concentration dependency of the binding amount of [$^3$H]-LY341495: Saturation binding of [$^3$H]-LY341495 (c, □). The results of quantification of LY379168 concentration-dependent competitive inhibition of binding of 100 nM [$^3$H]-LY341495 to mGluR3 in the absence of MNI137 (c, d, ○) or in the presence of 1 μM MNI137 (d, □). All data are shown as mean±standard error (n=3). The analytical results of mGluR3-expressing membrane fraction prepared on the same day are shown in the same panel. *: A point where a significant difference with respect to the leftmost point is observed in each curve in (c) (p<0.01; t-test, two-tailed). No significant difference due to the presence or absence of 1 μM MNI137 was observed in (d) (p>0.05; t-test, two-tailed). (e and f) Ligand concentration dependency of G protein activation efficiency by mGluR3-expressing membrane fraction: LY341495 (■) or LY379268 (●) concentration-dependent changes in the absence of other ligands are shown in (e). LY379268 concentration dependency in the presence of 100 nM LY341495 and the absence of MNI137 (●) or in the presence of 100 nM LY341495 and 1 μM MNI137 (■) is shown in (f). ○ and □ show negative controls obtained by measuring the G protein activation efficiency by a mock transfected plasma membrane fraction under the same ligand condition. All data are shown as mean±standard error (n=3 to 5). *, #: A point where a significant difference with respect to the leftmost point is observed in each curve in (e) (*: p<0.01, #: p<0.03; t-test, two-tailed). **: A point where a significant difference is observed between two curves (in the presence or absence of 1 μM MNI137) in (f) (p<0.01; t-test, two-tailed). (g) Comparison of $D_{Av}$ and G protein activation efficiency in the presence or absence (+/−) of each ligand at a certain concentration (+: 100 μM LY379268, 100 nM LY341495, and 1 μM MNI137). All data were normalized by defining a condition characterized by the presence of 100 nM LY341495 and the absence of other ligands as 0% and a condition characterized by the presence of 100 μM LY379268 and the absence of other ligands as 100%. All data are shown as mean±standard error ($D_{Av}$: n=20 cells, G protein activation efficiency: n=3 to 5).

The average value $D_{Av}$ of the diffusion coefficients of mGluR3 molecules was calculated from the MSD-Δt plot and was plotted with respect to each ligand concentration (FIG. 4(a, b)). When other ligands are not present, the $D_{Av}$ increased depending on the concentration of LY341495 and decreased depending on the concentration of LY379268 (FIG. 4(a)). In the presence of 100 nM LY341495, the LY379268 concentration-dependent decrease of the $D_{Av}$ was more markedly observed. In contrast, under conditions further adding 1 μM MNI, the LY379268 concentration-dependent decrease of $D_{Av}$ was suppressed, and a significant change was not observed (FIG. 4(b)). Subsequently, in order to verify the relationship between the concentration dependency of the change of $D_{Av}$ and the ligand affinity, a [$^3$H]-LY341495 binding experiment was performed using a HEK293 membrane fraction expressed mGluR3 under similar ligand conditions. The $EC_{50}$ (28.2±0.9 nM in FIG. 4(a), mean±SEM, n=20 cells) of the LY341495 dependent change of $D_{Av}$ was a similar value to the binding affinity (47.4±1.7 nM in FIG. 4(c), n=3) of [$^3$H]-LY341495. The $IC_{50}$ of the LY379268 dependent change of $D_{Av}$ did not vary regardless of whether 100 nM LY341495 was present or absent (1.19±0.02 and 1.03±0.08 μM in FIG. 4(a) and FIG. 4(b), respectively, n=20 cells). The differences among these values were less than two-fold the affinity (0.55±0.08 μM in FIG. 4(c), n=3) of LY379258 to mGluR3 estimated from the competitive binding experiment of LY379268 and 100 nM [$^3$H]-LY341495. Accordingly, the ligand concentration dependency of the $D_{Av}$ of mGluR3 well corresponded to the ligand binding affinity. In addition, 1 μM MNI137 did not influence the binding affinity of LY379268 (FIG. 4(d)).

Subsequently, a [$^{35}$S]-GTPγS binding experiment was performed using a HEK293 membrane fraction expressed mGluR3 and purified $G_o$ protein, and the ligand concentration dependency of the G protein activation ability of mGluR3 was analyzed (FIG. 4(e, f)). As a result, it was revealed that mGluR3 shows very high G protein activation ability even under ligand-free conditions and this constitutive activity is suppressed depending on the concentration of LY341495 (FIG. 4(e)). This result was consistent with the past finding that binding of a chloride ion to the ECD of mGluR3 is a factor of the high constitutive activity[5,6]. Accordingly, it was believed that the ligand-dependent change of $D_{Av}$ observed in FIG. 4(a) reflects the ligand-dependent change in the proportions of the inactive state and the active state of mGluR3 molecules on a living cell membrane. Furthermore, it was confirmed that 1 μM MNI137 suppresses the LY379268-dependent increase of G protein activation ability (FIG. 4(f)). This well corresponded to the suppression of the change of $D_{Av}$ by addition of 1 μM MNI137 (FIG. 4(b)).

The $IC_{50}$ (2.11±0.18 nM in FIG. 4(e), n=3) of the LY341495-dependent suppression of the G protein activation ability of mGluR3 showed one order of magnitude lower value than the concentration dependency of the change of $D_{Av}$ and the ligand affinity. In the absence of other ligands, the $EC_{50}$ (0.025±0.0029 μM in FIG. 4(e), n=3) of the LY379268-dependent increase of the G protein activation ability of mGluR3 showed two orders of magnitude lower value than the concentration dependency of the change of $D_{Av}$ and the ligand affinity. In general, the ligand concentration dependency ($EC_{50}/IC_{50}$ by a known method that measures a downstream change of the receptor shows a lower value compared to the ligand affinity in some cases. This is caused by that amplification occurs in each process of signaling and the cell response is thereby saturated only by binding of a ligand to a few receptors. Accordingly, in the known method, it was difficult to estimate the occupancy rate of the ligand from the cell response. In contrast, in single-molecule dynamics analysis, since the change of the diffusion coefficient of the receptor molecule itself is quantified, no amplification occurs, and the change of the proportions of the inactive state and the active state can be captured. It was accordingly believed that the $EC_{50}/IC_{50}$ value was similar to that of the ligand affinity.

1-2. Ligand-Dependent Change of Diffusion State Distribution of mGluR3

Figure 5:
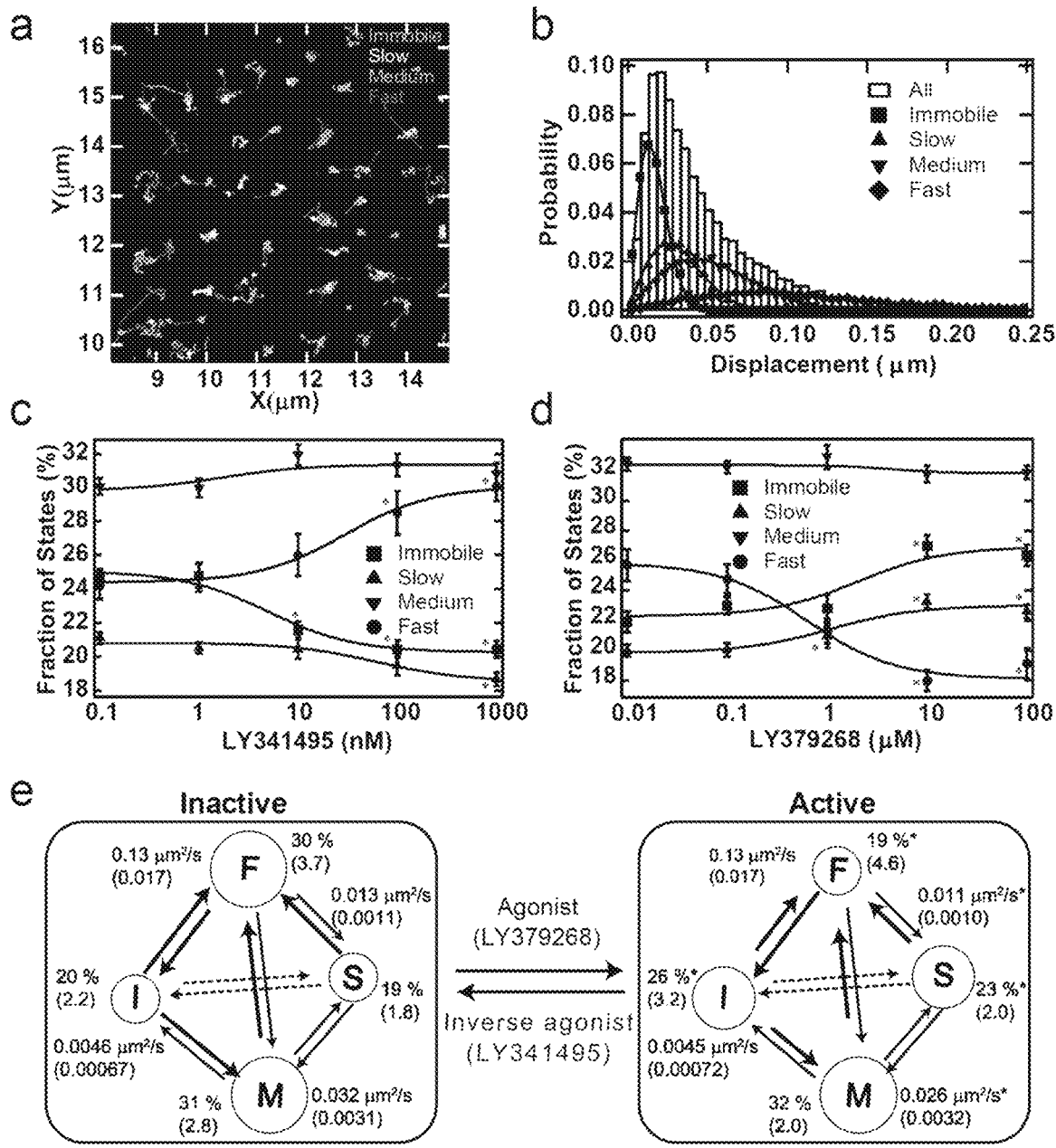
FIG. 5 shows VB-HMM analysis of the tracks of mGluR3. (a) Steps of the tracks in FIG. 1(b) were classified into four diffusion states. Immobile, slow, medium, and fast diffusion states were indicated in blue, yellow, green, and red, respectively. (b) The histograms of the displacements in 30.5 ms of all tracks (black bar; 28,092 steps, 573 tracks) were classified into four diffusion states by VB-HMM analysis. The immobile, slow, medium, and fast diffusion states are each shown. The histogram of the displacement in each state was fitted by Expression 6 shown in the paragraph "Method" described below. (c and d) Ligand concentration-dependent change in the proportion of each diffusion state. LY341495 concentration-dependent change is shown in (c). LY379268 concentration-dependent change in the presence of 100 nM LY314195 is shown in (d). The immobile, slow, medium, and fast diffusion states are each shown. All data are shown as mean±standard error (n=20 cells). *: A point where a significant difference with respect to the leftmost point is observed in each curve (p<0.01; t-test, two-tailed). (e) Transition diagram between the inactive (1 μM LY314195) and active (100 μM LY379268, 100 nM LY341495) ligand conditions of the four diffusion states of mGluR3. The diffusion coefficient and the proportion of each diffusion state are shown next to the circle. The size of each circle reflects the proportion. The standard error (n=20 cells) is indicated in parentheses. The length of each arrow between the states reflects the rate constant calculated from the time constant in FIG. 7. State transition showing a significant difference in the time constant between the two conditions in FIG. 7 is indicated with a thick arrow. *: Diffusion coefficient and proportion showing a significant change for the inactive ligand condition (p<0.01; t-test, two-tailed).
Figure 6:
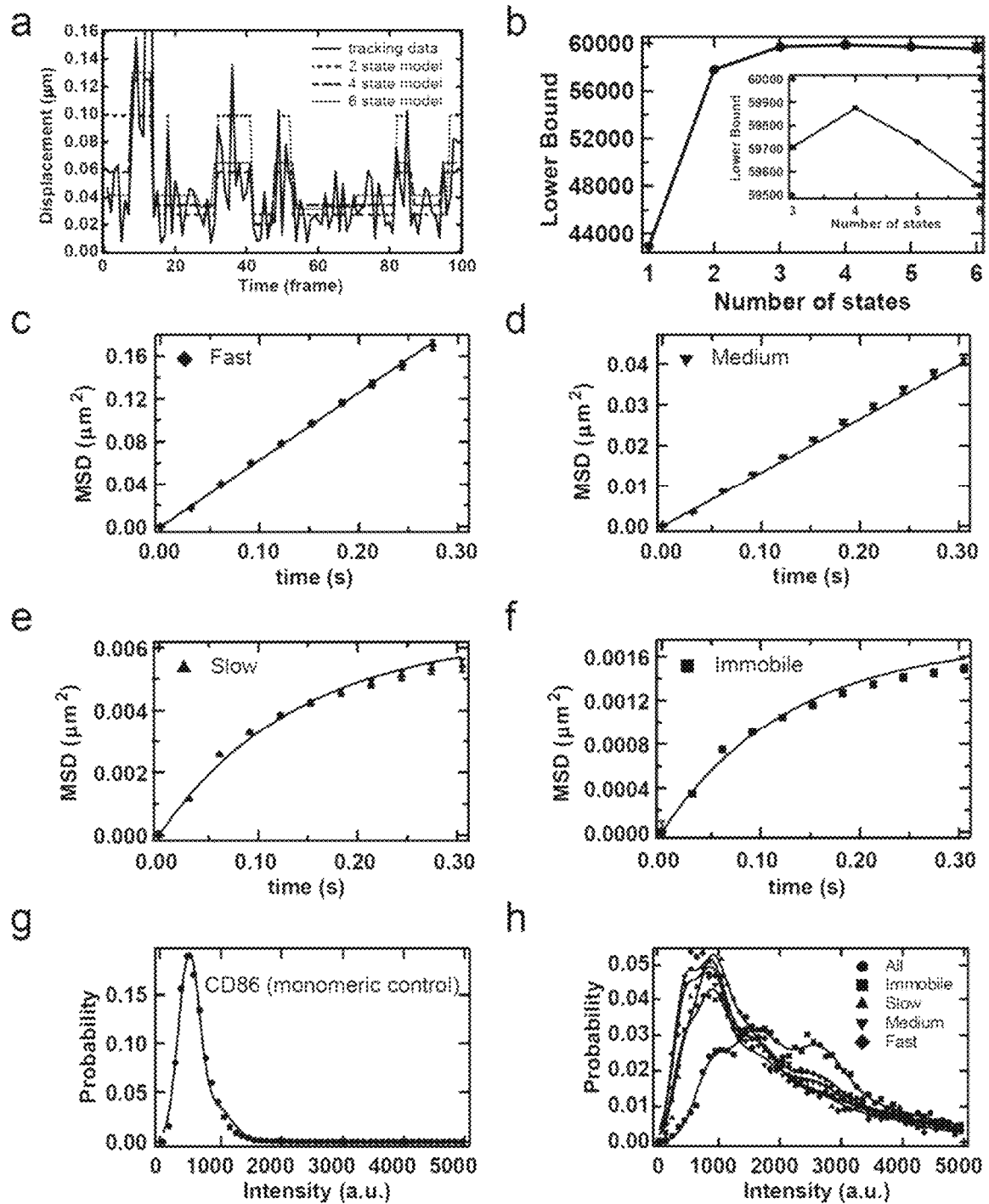
FIG. 6 shows an example of VB-HMM analysis for tracks of mGluR3. (a) The results of clustering analysis for time series changes (tracking data) of the displacement between frames in mGluR3 molecule one track are shown with models of 2, 4, and 6 states. (b) Comparison of likelihood in clustering analysis of the data of the same cells with states of different numbers. The number of state showing the highest lower limit of variation is estimated to be most probable in the VB-HMM analysis. An enlarged view of clustering analysis with models of 3 to 6 states is shown in the inset. The 4 state model showed the highest lower limit of variation. (c to f) MSD-Δt plots of the data of the same cells in FIG. 5(a, b) at each diffusion state. In the fast (c) and medium (d) states, the plots are linear and cannot be distinguished from that of free diffusion in the average movement of the receptor. In contrast, in the slow (e) and immobile (f) states, the plots show upward convex shapes and suggest limited diffusion of the receptor. The data are shown as mean±standard error (immobile: 7760 steps, slow: 5278 steps, medium: 7009 steps, fast: 4708 steps). (g) Intensity distribution of TMR-labeled CD86 measured under the same conditions as those in mGluR3: monomer control. (h) Intensity distributions of TMR-labeled mGluR3 in the same cells in FIG. 5(a, b). The data of each of the immobile, slow, medium, and fast diffusion states and all tracks are shown. The intensity distribution histograms (g, h) were fitted by the sum of Gaussian functions (Expression 7 shown in the paragraph "Method" described below).

One major advantage of single-molecule measurement is that it is possible not only to compare the mean values of the diffusion coefficients but also to compare the distributions of the quantified movement and intensity of individual receptor molecules. Accordingly, the present inventor performed clustering analysis of the diffusion state of each track of mGluR3 molecules based on variational Bayesian method-hidden Markov model (VB-HMM)[8,9]. The results suggested that the movement of mGluR3 molecules in a living cell membrane is classified into four different diffusion states (immobile, slow, medium, and fast) (FIGS. 5 and 6). Furthermore, intensity distribution histogram of each diffusion state was formed, and the apparent multimer size was estimated by extrapolation with a mixed Gaussian function. Membrane protein CD86[10], which is known to be present as a monomer, was similarly expressed in HEK293 cells, and the fluorescence intensity per one molecule of TMR was estimated from the results of measurement of TRM-labeled cells (FIG. 6(g)). As a result, the intensity giving the maximum value of the intensity distribution histogram of mGluR3 was estimated to be about twice that of CD86, and it was confirmed that mGluR is mostly present as a dimer (FIG. 6(h)). Furthermore, the intensity distribution histogram of mGluR3 in the immobile state shifted toward the right compared to those in other diffusion states, which suggested that higher order multimers are generated in conjunction with a decrease in diffusion coefficient (FIG. 6(h)).

Figure 7:
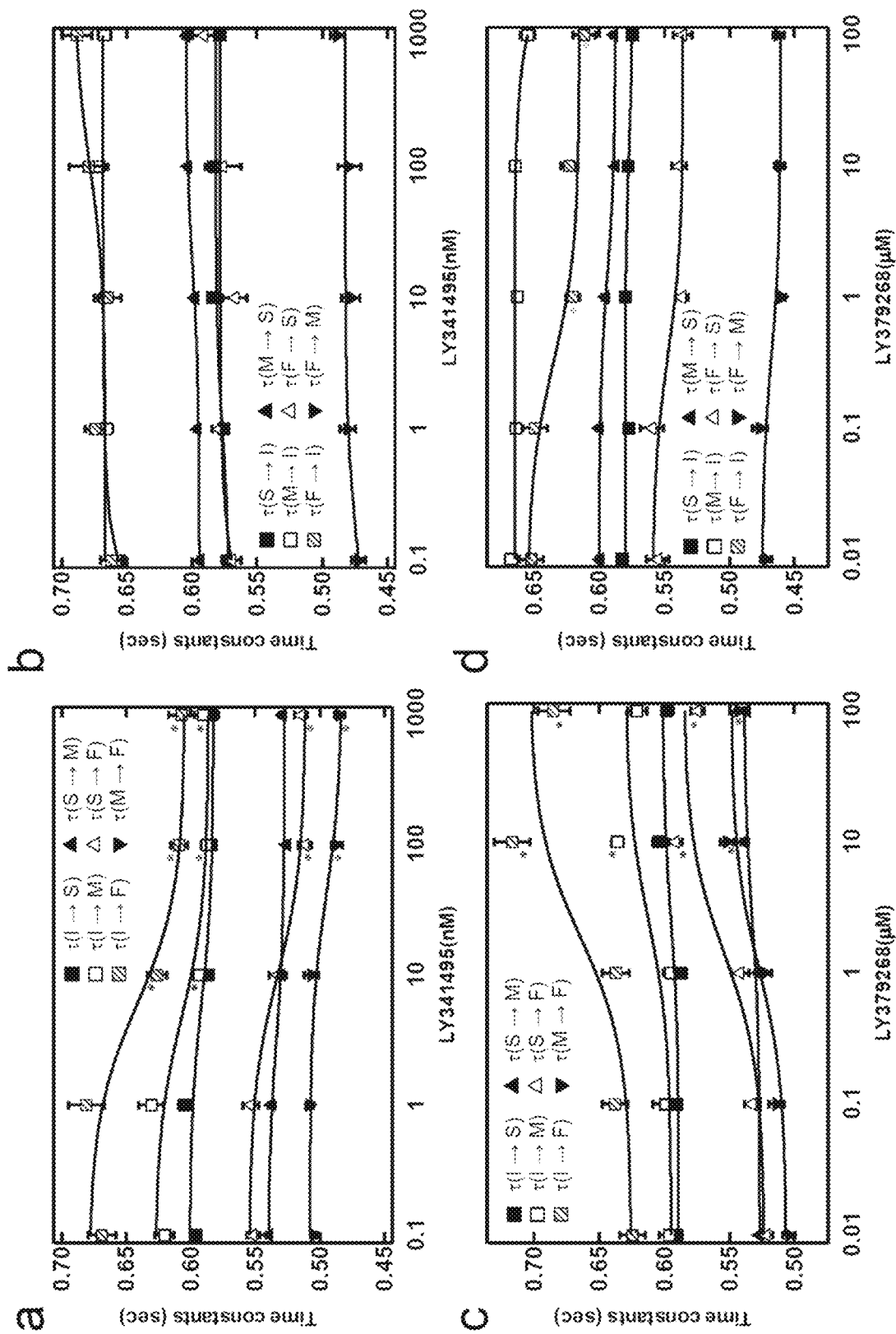
FIG. 7 shows ligand concentration-dependent changes of time constant in transition between diffusion states. The time constant of transition between diffusion states was estimated from the state transition probability in one frame (30.5 ms) of VB-HMM analysis. (a and b) LY341495 concentration dependency; (c and d) LY379268 concentration dependency in the presence of 100 nM LY314195; (a and c) Time constants of transition from slower diffusion state to faster diffusion state; (b and d) Time constants in reverse reaction of (a and c). All data are shown as mean±standard error (n=20 cells). *: A point where a significant difference with respect to the leftmost point is observed in each curve (rate of change ≥3% and p<0.01; t-test, two-tailed).
Figure 8:
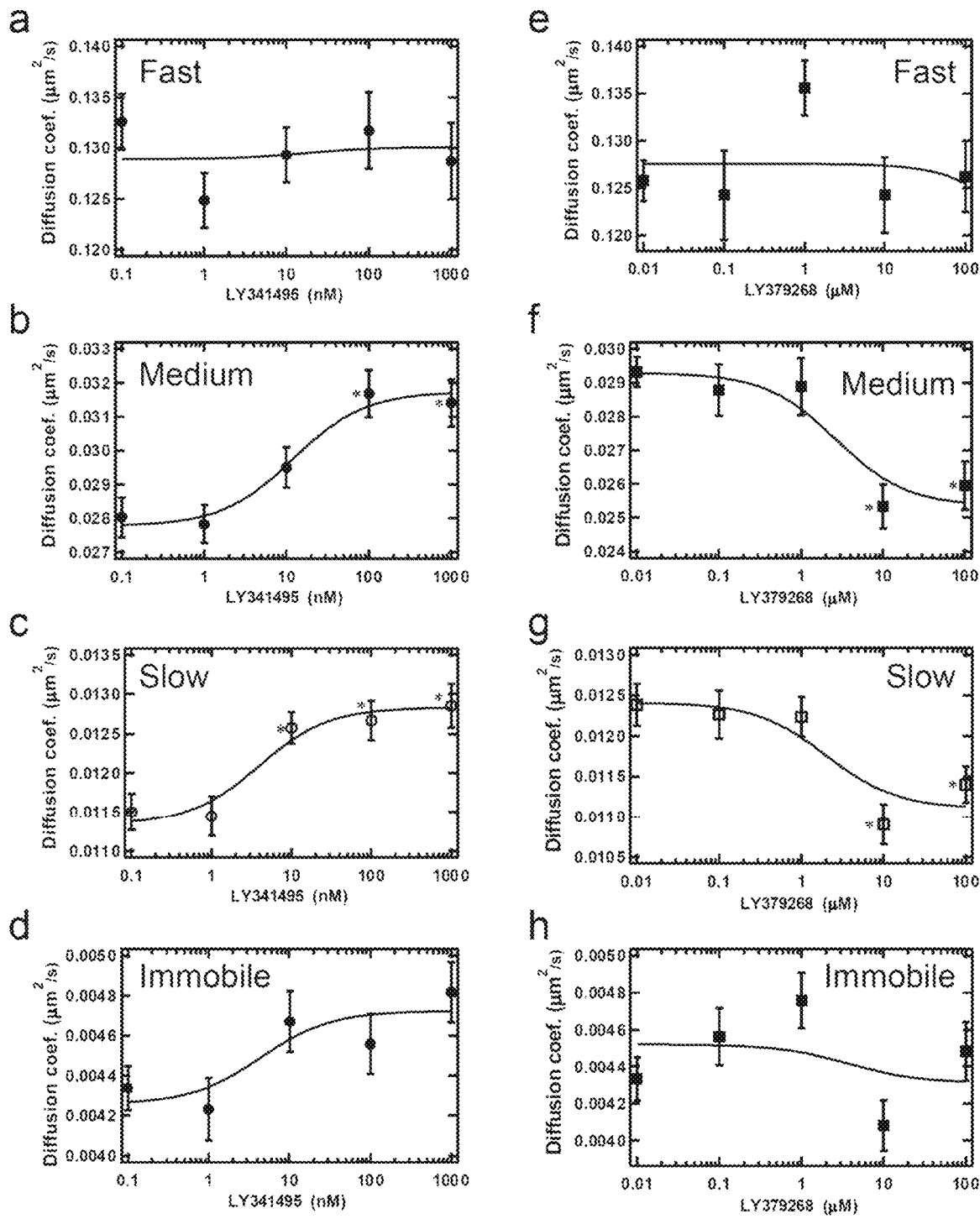
FIG. 8 shows the ligand concentration-dependent change in the diffusion coefficient of each diffusion state. The diffusion coefficient of each diffusion state estimated from the displacement in one frame (30.5 ms) of VB-HMM analysis. The LY341495 concentration dependency is shown for each of the fast (a), medium (b), slow (c), and immobile (d) states. The LY379268 concentration dependency in the presence of 100 nM LY314195 is shown for each of the fast (e), medium (f), slow (g), and immobile (h) states. All data are shown as mean±standard error (n=20 cells). *: A point where a significant difference with respect to the leftmost point is observed in each curve (p<0.01; t-test, two-tailed).

The ligand-dependent changes of the proportions of the diffusion states were analyzed, and it was demonstrated that the proportion of the fast state increases, whereas the proportions of the immobile and slow states decrease, depending on the concentration of LY341495 (FIG. 5(c)). In contrast, LY379268 concentration dependently, increases in the immobile and slow states and a decrease in the fast state were significantly recognized. In estimation of the time constant of the transition between diffusion states from the transition matrix of VB-HMM analysis, a ligand-dependent change was recognized in the transition from a slower diffusion state to a faster diffusion state (FIG. 5(e), FIG. 7). This was a result that activated mGluR3 is trapped in some membrane domain and suggests a possibility that a slower diffusion state easily remains. In each diffusion state, in analysis of the ligand concentration dependency of the average diffusion coefficient, an activation-dependent decrease in average diffusion coefficient was recognized in the medium and slow states (FIG. 5(e), FIG. 8). Through comprehensive consideration of the above, the ligand-dependent changes of $D_{Av}$ shown in FIG. 4(a, b) were believed to be derived from the changes of the proportions of the fast state and the slow and immobile states in the directions opposite to each other and the changes of the average diffusion coefficients of the medium and slow states.

1-3. Influence of Pertussis Toxin on Diffusive Dynamics of mGluR3

Figure 9:
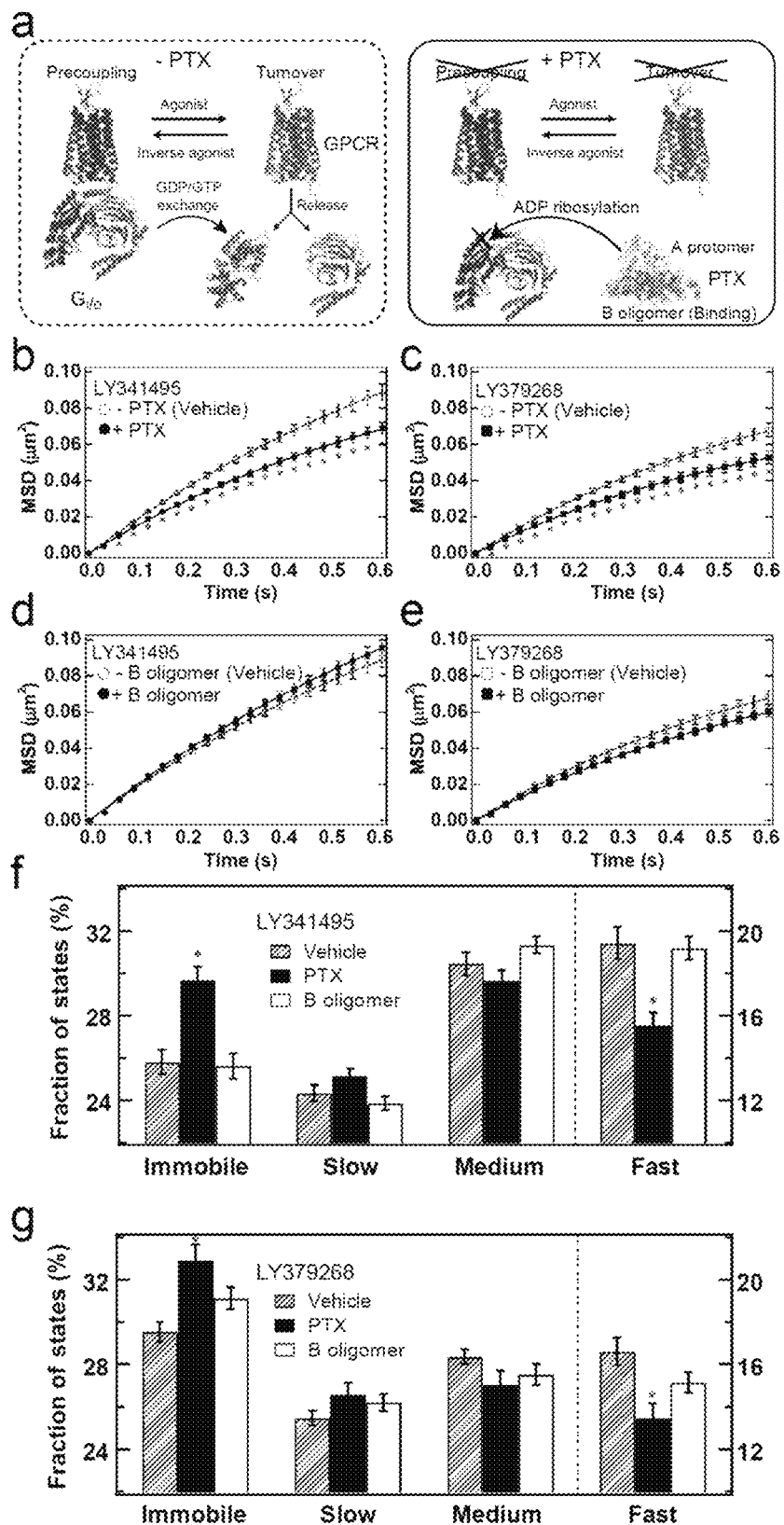
FIG. 9 shows influence of PTX treatment on the diffusive dynamics of mGluR3. (a) Scheme views of the influence of PTX treatment on the GPCR-$G_{i/o}$ protein interaction. When the PTX treatment is not performed, a certain amount of the GPCR is precoupled with $G_{i/o}$ protein even in the inactive state. With the activation of the GPCR, the exchange reaction between GDP and GTP of $G_{i/o}$ protein is accelerated, and the $G_{i/o}$ is dissociated from the GPCR. During the active state of the GPCR, primary binding to and dissociation from a plurality of $G_{i/o}$ molecules are repeated to accelerate the enzyme reaction. In contrast, after PTX treatment, $G_{i/o}$ protein is ADP-ribosylated to completely inhibit the GPCR-$G_{i/o}$ protein interaction in both the inactive and active conditions. The crystal structures (GPCR: 4OR2, trimeric G protein: 1GP2, G-α subunit: 1GIA, PTX: 1PRT) in the drawing were drawn with PyMol. (b to e) Comparison of MSD-Δt plots of the tracks of mGluR3 with and without PTX treatment. MSD-Δt plots in the inactive ligand condition (100 nM LY314195) and in the active ligand condition (100 μM LY379268) are shown in (b) and (c), respectively. Comparison of MSD-Δt plots with and without PTX B-oligomer treatment in the same ligand conditions are also shown in (b) and (c), respectively. *: A point where a significant difference in MSD was observed compared to vehicle treatment (p<0.01; t-test, two-tailed). (f and g) Comparison of the proportions of diffusion states estimated from VB-HMM analysis in the same tracks as those in (b to e). Comparison in the inactive ligand condition is shown in (f), and comparison in the active ligand condition is shown in (g). *: A point where a significant difference in proportion was observed compared to vehicle treatment (p<0.01; t-test, two-tailed). All the experimental results in (b to g) are shown as mean±standard error (n=20 cells).

In order to verify whether the diffusion state of mGluR3 interacting with G protein correlates with any of the above four states, $G_{i/o}$ protein inhibition experiment using pertussis toxin (PTX) was performed (FIG. 9(a)). When $G_{i/o}$ protein was inhibited by PTX treatment, the mean value of the diffusion range of mGluR3 was significantly decreased both in the presence of 100 nM LY341495 and in the presence of 100 μM LY379268 (FIG. 9(b, c)). In addition, as the results of VB-HMM analysis, it was estimated that these changes in the average value were caused by a decrease in the fast state and an increase in the immobile state (FIG. 9(f, g)). In order to verify whether this influence of the PTX treatment was caused by the inhibition of the interaction between $G_{i/o}$ protein and mGluR3, the influence of the B-oligomer of PTX was analyzed as negative control. PTX is composed of an A-protomer (S1 subunit) and a B-oligomer (S2-S5 subunit) (FIG. 9(a)). Although the B-oligomer plays a role of binding to the sugar chain of ganglioside on a cell membrane and incorporating the A-protomer into the cell, it is also known that the B-oligomer itself activates a G protein-independent signaling pathway[11]. The A-protomer incorporated into the cell ADP-ribosylates the $G_{i/o}$ α-subunit and inhibits the $G_{i/o}$ protein from binding to the receptor[11]. The changes of the diffusion range and the proportions of diffusion states of mGluR3 observed by the above-described PTX treatment were not caused by treatment with B-oligomer only (FIG. 9(d to g)).

Accordingly, the ADP-ribosilation of $G_{i/o}$ by the A-protomer was estimated to be a factor lowering the diffusion of mGluR3. The results above suggested that many of the mGluR3 molecules interacting with $G_{i/o}$ are present in the fast state and that a decrease in the diffusion range is caused by a reduction in the fraction by PTX treatment. Since the PTX-dependent change in the diffusion of mGluR3 was detected not only in the presence of an agonist but also in the presence of an inverse agonist, it was assumed that mGluR3 interacts with $G_{i/o}$ even under the inactive state. Precoupling between a GPCR in the inactive state and G protein has been reported in the past in some receptors and is believed to play an important role for rapid cell response after ligand stimulation[12-14]. Although the activation of mGluR3 accelerates the separation of precoupled $G_{i/o}$ in the inactive state, this resembles the influence on the binding inhibition between mGluR3 and $G_{i/o}$ by PTX treatment in that the proportion of mGluR3 binding to $G_{i/o}$ is decreased (FIG. 9(a)). Accordingly, it was estimated that one factor of activation-dependent decrease of the $D_{Av}$ of mGluR3 is a decrease in the proportion of mGluR3 interacting with $G_{i/o}$.

1-4. Analysis of Interaction Between Clathrin and mGluR3 by Two-Color Single-Molecule Imaging Subsequently, it was verified what kind of physiological function corresponds to the immobile state increased by activation of mGluR3. In long-time single-molecule measurement of mGluR3, it was observed that light bright spots showing slow diffusion were formed and the bright spots then disappeared at once with fast directional movement. This was probably caused by that the bright spots deviated from the range of the total internal reflection illumination and thereby disappeared when mGluR3 formed clusters and were then transported into cells by endocytosis. Since a clathrin coated vesicle (CCV)-dependent path is known (FIG. 10(a)) as a general mechanism of endocytosis of a GPCR, colocalization was investigated by two-color single-molecule imaging using GFP-labeled clathrin light chain (CLC) and TMR-labeled mGluR3. As a result, it was observed that mGluR3 was colocalized with CLC; the fluorescence intensity of TMR then sharply increased; colocalization continued for several seconds; and the fluorescence intensities of TMR and GFP then simultaneously largely decreased (FIG. 10(b, c)). This probably captured the situation of the endocytosis through accumulation of the mGluR3 clusters in a clathrin coated pit (CCP) and then formation of a CCV. It was observed that the same endocytosis is repeated in the same domain, suggesting a possibility of the presence of a specific membrane domain where a CCP is readily formed.

Figure 10:
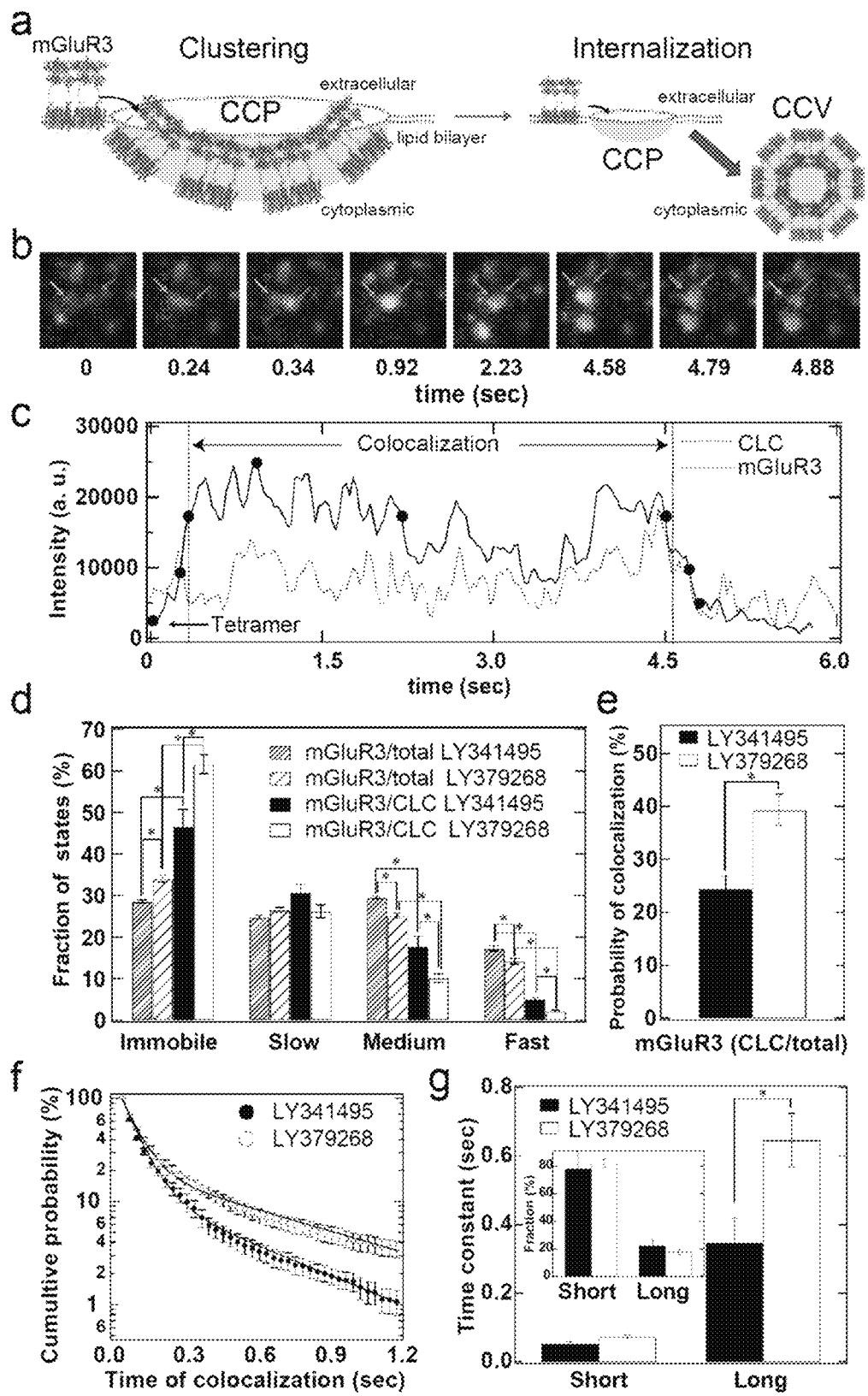
FIG. 10 shows colocalization analysis of mGluR3 and CLC. (a) Scheme views of mGluR3 that clusters in CCP and is endocytosed. (b) A typical example of colocalization of TMR-labeled mGluR3 (red) and GFP-labeled CLC (green). Colocalization of mGluR3 with CLC is recognized after 0.34 seconds. (c) Change in intensity of particles indicated by the red and green arrows in (b). The intensity of TMR-labeled mGluR3 rapidly increases in synchronization with the colocalization with GFP-labeled CLC, and the intensities of TMR and GFP simultaneously decrease after 4.5 seconds. (d) Comparison of proportions of diffusion states estimated from VB-HMM analysis. The proportions of the diffusion states estimated from the all tracks of mGluR3 in the inactive ligand condition (100 nM LY314195) and the active ligand condition (100 μM LY379268) are shown by shaded bars. The proportions of the diffusion states estimated from the tracks of mGluR3 colocalized with CLC are shown by black or white bars. (e) The proportions of the tracks of mGluR3 colocalized with CLC in the inactive ligand condition (100 nM LY314195) and the active ligand condition (100 μM LY379268) for all tracks are shown. (f and g) Cumulative frequency distributions of colocalization time of mGluR3 and CLC were compared in the inactive ligand condition (LY341495) and the active ligand condition (LY379268). The curves in (f) were fitted by a two-component exponential function (Expression 8 shown in the paragraph "Method" described below), and the time constants and component ratios (inset) are shown in (g). All data in (d to g) are shown as mean±standard error (inactive condition: n=15 cells, active condition: n=18 cells). *: Significant difference between the conditions (p<0.01; t-test, two-tailed).

Subsequently, the present inventor analyzed the proportions of diffusion states of mGluR3 molecules colocalized with CLC (mGluR3/CLC) and compared the proportions with the proportions of diffusion states of the total mGluR3 molecules (mGluR3/total) (FIG. 10(d)). As a result, it was demonstrated that the proportion of immobile state of the mGluR3/CLC was significantly high compared to that of the mGluR3/total. Accordingly, it was revealed that the diffusion of mGluR3 molecules is slowed with binding to clathrin. Comparison of the inactive state (on stimulation with 100 nM LY341495) and the active state (on stimulation with 100 μM LY379268) revealed that in the active state, compared to the inactive state, the proportion of the immobile state of the mGluR3/CLC is increased (FIG. 10(d)). Furthermore, it was revealed that the colocalization probability of mGluR3 and CLC and the colocalization time constant are significantly increased with activation (FIG. 10(e to g)). Two, Short and Long, time constants and proportions thereof were estimated by extrapolation of a double exponential function to the cumulative frequency distributions of colocalization time of mGluR3 and CLC (FIG. 10(f, g)). Since no activation-dependent change was observed in the Short-time constant, mGluR3 probably contains a fraction accidentally located near the CLC. In constant, the Long-time constant was increased by about two-fold by activation (FIG. 10(g)). Since the ratio of the Short and the Long did not activation dependently change (FIG. 10(g), inset), it was believed that the increase of about 1.6-fold in the colocalization probability shown in FIG. 10(e) was mainly derived from the increase of the colocalization time. Comprehensive consideration of the results above revealed that the increase in the immobile state of mGluR3 due to activation is partly attributable to an increase of the mGluR3 molecules interacting with clathrin.

Figure 11:
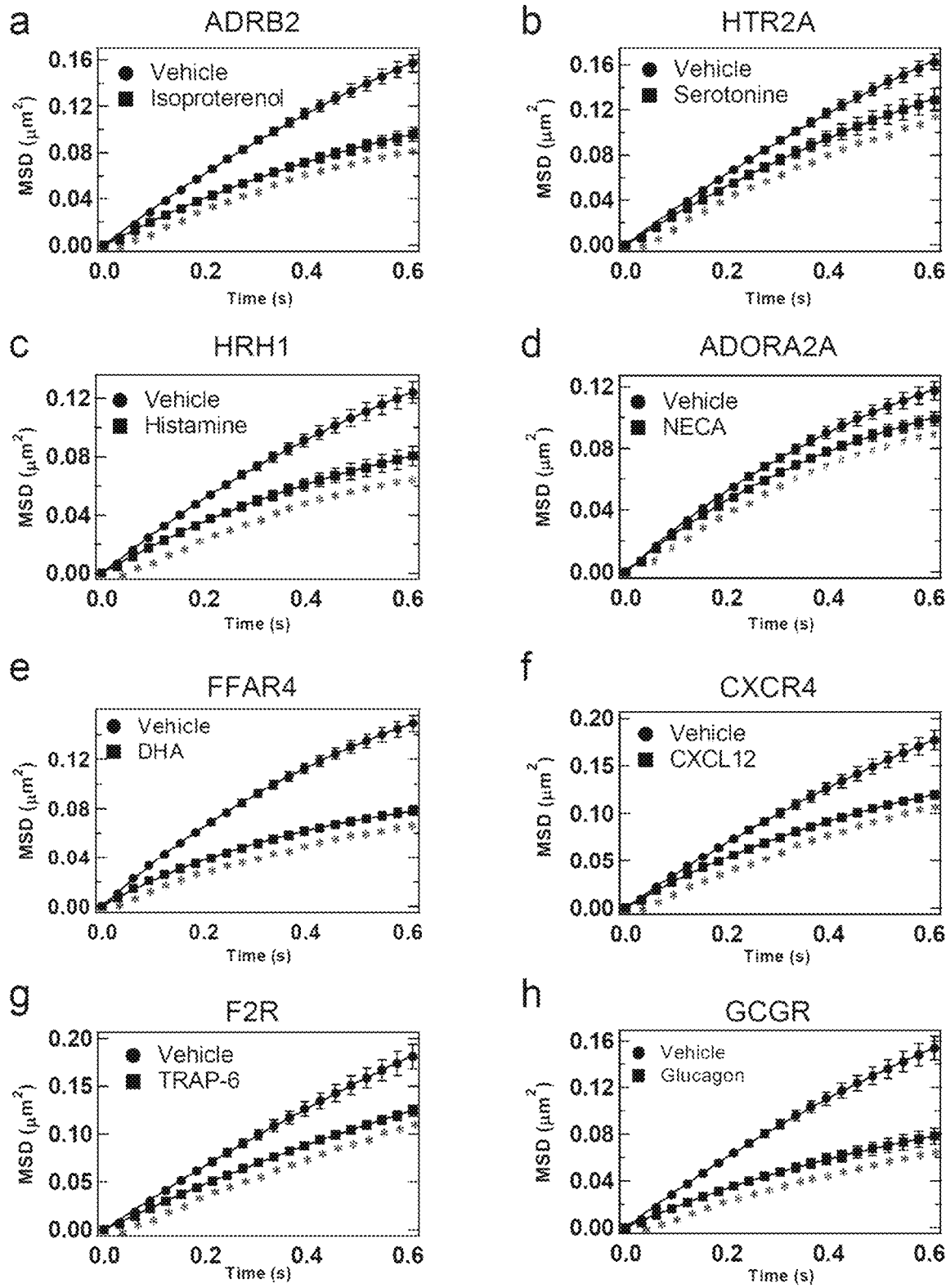
FIG. 11 shows the changes in MSD-Δt plot of the track of a GPCR stimulated with an agonist. MSD-Δt plots of (a) ADRB2, (b) HTR2A, (c) HRH1, (d) ADORA2A, (e) FFAR4, (f) CXCR4, (g) F2R, and (h) GCGR labeled with STELLA Fluo 650 in HEK293 cells. In each receptor, the plots indicated by ■ are those when an agonist was added, and the plots indicated by ● are those when a vehicle was added. All data are shown as mean±standard error (n=20 cells). *, #: A point where a stimulation-dependent significant difference in each Δt is observed (*: p<0.01, #: p<0.03; t-test, two-tailed).

1-5. Generality of Agonist-Dependent Change of Diffusive Dynamics in Other GPCRs In order verify the generality of a relationship between the activation and diffusive dynamics change of a GPCR, eight GPCRs belonging to other family were also fluorescence labeled at the C-terminus and were subjected to single-molecule imaging. In the presence or absence of an agonist of each GPCR, single-molecule imaging was performed for 20 cells, the bright spot of each receptor molecule was tracked, and MSD-Δt plots were compared (FIG. 11). Furthermore, $D_{Av}$ was calculated from the MSD-Δt plots, and a list was formed in Table 1. As a result, an agonist-dependent decrease of diffusion coefficient was significantly recognized in all verified GPCRs (FIG. 11, Table 1). Accordingly, it was believed that the estimation of activity of a GPCR based on the single-molecule diffusive dynamics is generally applicable regardless of the molecular systematic position of the receptor, the chemical properties of the ligand, and the subtype specificity of G protein to be conjugated. In the absence of the ligand, the DA (0.047 μm²/s) of mGluR3 was lower than the $D_{Av}$ (0.06 to 0.09 μm²/s) of other GPCRs, and the latter value was close to the $D_{Av}$ (0.064 μm²/s) of mGluR3 in the presence of 1 μM LY341495. Accordingly, the main reason of the slow diffusion of mGluR3 in the absence of the ligand is probably the high constitutive activity shown in FIG. 4(e). In the presence of an agonist, the $D_{Av}$ of a GPCR was within a range of 0.04 to 0.07 μm²/s. Although the agonist-dependent lowering rate of $D_{Av}$ of each GPCR was 13% to 44%, it is detectable with a p value of $8.7×10^{-11} < p < 9.1×10^{-3}$ by Welch's t-test (n=20 cells, two-tailed), and by using this method, high accuracy detection of the effect of a drug to various GPCRs can be expected. (Accordingly, if there is a difference of about 13% when 20 cells were measured in each of the respective ligand conditions, it may be possible to detect the change at a significance level of p<0.01 based on the Welch's t-test (two-tailed).) Although the absolute value of $D_{Av}$ varies depending on the type of the GPCR, the $D_{Av}$ of mGluR3 is lower than those of other GPCRs in both the inactive and active states. Accordingly, dimerization may also be a factor of slowing the diffusion of a GPCR.

the proportions of four diffusion states of mGluR3 and the diffusion coefficient in each state (FIG. 5(e)). The G protein inhibition experiment by PTX treatment suggested that the fast state includes a state of mGluR3 being bound to G protein (FIG. 9). Furthermore, colocalization analysis of clathrin and mGluR3 demonstrated that the immobile state includes a state of mGluR3 being bound to clathrin in a large amount (FIG. 10). The results above suggested that the changes of the functional states of mGluR3, such as activation-dependent cancellation of precoupling with G protein and binding to clathrin, are caused in conjunction with change of the diffusion state. As a factor defining the diffusion range of a membrane protein, the presence of a membrane skeleton backed by actin has been indicated by past single-molecule imaging analysis[15]. In the past, in single-molecule imaging analysis of M1-muscarine receptor[16], β-adrenaline receptor[10], and $GABA_B$ receptor[10], MSD-Δt plots are all linear as average, and free diffusion is supported. In contrast, in the Example, the MSD-Δt plots of tracks of mGluR3 show upward convex shapes, and the results suggested that the diffusion of receptor molecules is partially restricted by the membrane skeleton (FIG. 1(c to e)). Furthermore, as the results of VB-HMM analysis, the MSD-Δt plots in the immobile and slow states clearly have upward convex shapes, and it was revealed that diffusion of mGluR3 molecules is partially restricted by membrane domains, such as a CCP.

As described above, although the experiment by PTX treatment suggested that the fast state of mGluR3 is related to the binding of G protein, the results were different from the expected results before conducting the experiment. This is because that it was thought that if mGluR3 binds to G protein only at the active state, the influence of the PTX treatment is not observed in the presence of an inverse

TABLE 1

Comparison of ligand-dependent changes of $D_{Av}$ of nine GPCRs belonging to molecular-systematically diverse positions

| GPCR | Class | Group | Cluster | Endogenous ligand | G protein selectivity | $D_{Av}$ (μm²/s) Vehicle | $D_{Av}$ (μm²/s) Ligand | t-test p value | Compounds tested |
|---|---|---|---|---|---|---|---|---|---|
| ADRB2 | A | α | amine | adrenaline | $G_s$ | 0.078 ± 0.0024 | 0.051 ± 0.0023 | 1.2E−09 | Isoproterenol (10 μM) |
| HTR2A | A | α | amine | serotonine | $G_q/G_i$ | 0.079 ± 0.0022 | 0.065 ± 0.0034 | 2.1E−03 | serotonine (10 μM) |
| HRH1 | A | α | amine | histamine | $G_q$ | 0.064 ± 0.0023 | 0.045 ± 0.0025 | 1.1E−06 | histamine (1 μM) |
| ADORA2A | A | α | MECA | adenosine | $G_s$ | 0.066 ± 0.0022 | 0.058 ± 0.0016 | 8.0E−03 | NECA (10 μM) |
| FFAR4 | A | α | melatonin | free fatty acid | $G_q$ | 0.083 ± 0.0025 | 0.048 ± 0.0073 | 3.5E−13 | DHA (100 nM) |
| CXCR4 | A | γ | chemokine | chemokine | $G_i$ | 0.087 ± 0.0034 | 0.068 ± 0.0017 | 1.7E−05 | CXCL12 (20 nM) |
| F2R | A | δ | purin | thrombin | $G_q/G_i/G_{12}$ | 0.084 ± 0.0041 | 0.060 ± 0.0017 | 1.4E−05 | TRAP-6 (10 μM) |
| GCGR | B | secretin | peptide | glucagon | $G_s/G_q$ | 0.075 ± 0.0028 | 0.042 ± 0.0025 | 8.7E−11 | glucagon (1 μM) |
| mGluR3 | C | — | amino acid | glutamate | $G_i$ | 0.047 ± 0.0022 | 0.039 ± 0.0018 | 9.1E−03 | LY379268 (100 μM) |
|  |  |  |  |  |  | 0.047 ± 0.0015 | 0.064 ± 0.0018 | 1.6E−08 | LY341495 (1 μM) |

The class, group, and cluster of a GPCR subjected to single-molecule measurement were listed according to past literatures[30, 31]. $D_{Av}$ of each GPCR other than mGluR3 was calculated based on MSD in FIG. 11 (Expressions 1 and 2 shown in the paragraph "Method" described below). All data are shown as mean ± standard error (n = 20 cells). The p value was calculated based on Welch's t-test (two-tailed) and indicates a significant difference between vehicle addition and ligand addition. The ligand used in stimulation on each GPCR and the concentration thereof are shown in the rightmost column.

2. Discussion

In this Example, a novel method for evaluating a medicinal effect by quantifying single-molecule diffusive dynamics of a GPCR on a living cell membrane was developed. The present inventor proved a concept of medicinal effect evaluation based on single-molecule imaging analysis by using the mGluR3 of Class C GPCR as a model. As a result, it was revealed that all the constitutive activity, agonist-dependent activation, inverse agonist-dependent inactivation, and negative allosteric ligand-dependent suppression of activation of mGluR3 can be quantified using $D_{Av}$ as an index (FIG. 4). The VB-HMM analysis suggested that these ligand-dependent changes of $D_{Av}$ are due to the changes of agonist, and a change occurs only in the presence of an agonist. However, actually, in the presence of an inverse agonist, a decrease in the fast state of mGluR3 associated with PTX treatment was more notably observed (FIG. 9). This result suggests that mGluR3 in the inactive state is precoupled with G protein, and it can be said that past findings were also supported by the single-molecule diffusive dynamics. The precoupling between a GPCR and G protein has been reported in the past in Class A receptors, such as an adrenaline receptor and a muscarinic acetylcholine receptor. A ternary complex model was proposed[17] more than 20 years ago based on that the presence of a receptor having high affinity to an agonist can be described by assuming the binding between a GPCR and G protein in the absence of a ligand, the model has been repeatedly expanded thereafter and now is accepted in a wide range of GPCRs. However, a biochemical method was difficult to clearly distinguish interaction with G protein due to constitutive activation of a GPCR from precoupling in the inactive state. After that, the binding between a GPCR and G protein was cell-biologically analyzed using fluorescence resonance energy transfer (FRET), and significant occurrence of the binding of the both was observed even under inactive conditions containing an inverse agonist at a saturation concentration to show precoupling[12,13]. The results of this Example were consistent with the past model suggesting that the precoupling state is rather stable than the ternary complex in the active state. It is unclear at present why the binding to G protein accelerates the diffusion of mGluR3. In the past, it was demonstrated that in astrocytes, the interaction between the C-terminal site of mGluR5 and a protein on the cytoplasm side plays an important role in overcoming the diffusion barrier separating between a cell body and a dendrite. It is shown that in also precoupling of a GPCR and G protein, the C-terminal site of a receptor plays an important role[14], and it was assumed that the probability of overcoming the diffusion barrier supporting a membrane domain is increased by similar reasons to those in the above-described example of mGluR5.

The accumulation of a GPCR to a CCP is a process of endocytosis that is commonly observed across the family of GPCRs. Colocalization analysis of clathrin and mGluR3 by two-color single-molecule imaging showed an increase in the immobile state of mGluR3 by the binding of clathrin. In the process of inactivation of a GPCR, the C-terminal site of the receptor is phosphorylated by GRK, and arrestin binds to the phosphorylated site[18]. Furthermore, the GPCR-arrestin complex is accumulated in a CCP by interaction of arrestin with clathrin and AP2[18]. In the past, analysis of clathrin-dependent endocytosis of Class A GPCRs, such as adrenaline receptor and opioid receptor, with a total internal reflection fluorescence microscope has been reported. In these reports, since cells highly expressing the receptor and clathrin were used, the bright spot of a single receptor molecule is not dissolved. In this point, the reports differ from this Example. However, since measurement with a reduced laser output is possible, a longer time domain has been observed. Analysis of time constant from the formation of one CCP particle until the endocytosis revealed that the GPCR incorporated in the CCP controls the cell membrane staying time of the CCP[19,20]. These findings were consistent with the results of this Example showing that the colocalization time constant of mGluR3 and CLC is elongated by stimulation with an agonist (FIG. 10(f, g)). In the moving image of single-molecule imaging, formation of a cluster of mGluR3 in an existing CCP is observed. It was assumed a possibility that direct interaction between transmembrane domains of mGluR is one of motive forces for this cluster formation. Biochemical analysis in the past shows that activation of mGluR2 changes the interface of a dimer or multimer and increases higher order multimers. Endocytosis after collection of the GPCR in existing CCPs can reduce the energy cost of cells, compared to sequential endocytosis through formation of CCPs around activated each receptor, and is probably desirable for the cells.

Although GPCRs have almost no amino acid sequence homology across the family, all GPCRs share a common structural motif of a seven-transmembrane domain including three cytoplasm loop regions and a C-terminal region and interact with common G protein, GRK, and arrestin. The physiological phenomenon of influencing the diffusion of a receptor found in this Example does not specifically occur in Class C GPCR. If a medicinal effect on an arbitrary GPCR can be estimated from a change in diffusive dynamics common to GPCRs, a medicinal effect on a downstream different GPCR or orphan receptor can be evaluated using a common index. Accordingly, in this Example, similar measurements were further carried out on GPCRs of various families, and the generality of agonist-dependent changes of diffusive dynamics was verified. As a result, an activation-dependent decrease in diffusion coefficient was observed in eight GPCRs that were analyzed regardless of the downstream signaling pathways of the GPCRs (Table 1, FIG. 11). Measurement and quantification of the single-molecule diffusive dynamics of a GPCR with a total internal reflection fluorescence microscope are possible in any receptor localizing in the cell membrane. Accordingly, it was considered that the method developed in this Example is usable for evaluating medicinal effects on many other GPCRs including about 100 orphan receptors.

3. Method 3-1. Reagent

[$^3$H]-LY341495 (1.28 TBq/mmol), LY341495, LY379268, NMI137, NECA, and serotonin were purchased from Tocris Cookson Ltd. Isoproterenol was purchased from Santa Cruz Biotechnology. DHA was purchased from Sigma-Aldrich Co. Ltd. CXCL12 was purchased from Thermo Fisher Scientific. TRAP-6 was purchased from Bachem. Glucagon was purchased from Cedarlane. [$^{35}$S]-GTPγS (37 TBq/mmol) was purchased from PerkinElmer Life Sciences, Inc. Histamine, PTX, and B-oligomer were purchased from Wako Pure Chemical Industries, Ltd. Human CD86 cDNA was purchased from OriGene Technologies, Inc.

3-2. Production of cDNA

A DNA sequence encoding HaloTag7 (Promega Corporation) was amplified by PCR and was fused to the C-terminal sequence of mouse mGluR3 using In-Fusion HD Cloning Kit (Clontech Laboratories, Inc.). In order to quantify the expression level of HaloTag-fused mGluR3 by Western blotting, the epitope sequence of a monoclonal antibody Rho 1D4 recognizing the C-terminus of bovine rhodopsin was added immediately after the HaloTag sequence. Complementary DNAs of mGluR3 were inserted into a pCAG-GS vector[21]. Complementary DNAs of other GPCRs (ADRB2, HTR2A, HRH1, ADORA2A, FFAR4, CXCR4, F2R, and GCGR) were purchased from Promega Corporation. The DNA sequences encoding the GPCRs were inserted into pFC14K HaloTag CMV Flexi Vector. A DNA sequence encoding CD86 (M1-R277) was amplified by PCR and was inserted into a pEGFP-N1 mammalian expression vector (Clontech Laboratories, Inc.). Separately, the DNA sequence of EGFP of the vector was replaced with HaloTag7. The cDNA of GFP-fused CLC was used as reported in the past[22].

3-3. Single-Molecule Imaging

HEK293 cells were cultured in a DMEM/F12 (Gibco) medium added with 15 mM HEPES (pH 7.3), 29 mM NaHCO$_3$, and 10% FBS at 37° C. in an environment containing 5% CO$_2$. On the day before the observation, the HEK293 cells on a 60-mm dish (IWAKI) with a cover glass (Matsunami Glass Ind., Ltd.) were transfected with a plasmid DNA (pDNA) of HaloTag-fused mGluR3 using Lipofectamine 3000 (Invitrogen). A transfection reagent and pDNA (pDNA (0.1 µg), P3000 reagent (0.2 µL), Lipofectamine 3000 reagent (2.5 µL), Opti-MEM (120 µL, Gibco)) were mixed, and the mixture was then left to stand at room temperature for 15 minutes and was added to HEK293 cells on the 60-mm dish containing DMEM/F12 (3 mL). In two-color single-molecule measurement, pDNA (0.02 μg) of GFP-fused CLC was transfected together with HaloTag-fused mGluR3. After culturing at 37° C. in an environment containing 5% $CO_2$ for 3 hours, the medium was replaced with DMEM (3 mL, Sigma) not containing phenol red and containing 10% FBS. After culturing overnight, the medium was replaced with 3 mL of DMEM containing 300 nM HaloTag TMR ligand (Promega Corporation) and not containing phenol red and FBS, followed by being left to stand at 37° C. in an environment containing 5% $CO_2$ for 30 minutes to specifically stain the HaloTag-fused mGluR3 of the HEK293 cells. Other GPCRs were stained using 30 nM STELLA Fluo 650 HaloTag ligand (Goryo Chemical, Inc.) instead of the TMR ligand. The STELLA Fluo 650 is a membrane-permeable dye having higher intensity and stability, and the image quality of single-molecule imaging was improved. In an inhibitor experiment, a final concentrations of 5 nM PTX and 5 nM B-oligomer or vehicle were added to DMEM, followed by culturing at 37° C. in an environment containing 5% $CO_2$ for 6 hours and then microscopic observation. In single-molecule imaging, the cover glass was placed in a metal chamber (Invitrogen) and was washed with 400 μL of Hanks' balanced salt solution (HBSS (Sigma); containing 15 mM HPEPS (pH 7.1) and not containing $NaHCO_3$) five times, followed by observation at room temperature (25° C.). TMR-labeled mGluR3 on the cell membranes of the HEK293 cells were excited with total internal reflection illumination on an inverted fluorescence microscope (TE2000, Nikon Corporation), and single-molecule imaging was performed. The excitation light source used for TMR was 100 mW laser of 559 nm (WS-0559-050, NTT Electronics Corporation); the excitation light source used for GFP was a 200 mW laser of 488 nm (Sapphire 488-200, Coherent, Inc.); and the excitation light source used for STELLA Fluo 650 was a 140 mW laser of 637 nm (OBIS 637, Coherent, Inc.). The objective lens used was PlanApo 60×, NA 1.49 (Nikon Corporation). TMR and GFP were observed with dichroic mirror FF493/574 (Semrock); and STELLA Fluo 650 was observed with ET Cy5 filter set (Chroma). The fluorescences of TMR and GFP were wavelength dependently separated with dichroic mirror 59004b (Chroma) in a two-optical path branching system (M202J, Nikon Corporation), were allowed to pass through a band pass filter (GFP: ET525/50m, TMR: ET605/70m, Chroma), and were then photographed simultaneously by two EM-CCD cameras (ImagEM, Hamamatsu Photonics K.K.). The images were enlarged by placing a 4× relay lens in the two-optical path branching system and adjusted such that the pixel size was 67 nm/pixel (512×512 pixels). The fluorescence images were taken with imaging software ImagEM HRD (Hamamatsu Photonics K.K.) at parameter setting (exposure time: 30.5 ms, EM gain: 200, spot noise reduction: on). When cells are fixed for evaluating the positional accuracy in single-molecule measurement of TMR-labeled mGluR3 and GFP-labeled CLC, a method reported in the past[23] was used. A 4% PFA, 0.2% glutaraldehyde, and PBS were added to the HEK293 cells on the cover glass, followed by treatment at room temperature for 30 minutes. The cells were then washed with HBSS five times and were observed through a microscope.

3-4. Image Analysis of Single-Molecule Imaging

The images taken by the single-molecule imaging were stored in multiple TIFF files (16 bit) and were image processed with ImageJ as follows. Background was removed by setting Rolling ball radius to 25 pixels, and two frame moving average processing was then performed using Running_ZProjector plugin (Vale Lab homepage, http://valelab.ucsfedu/~nstuurman/ijplugins/). The images simultaneously photographed with two cameras were corrected for the positional error between two channels using Grid-Aligner plugin (Vale Lab homepage). A scattering image of a sample prepared by spreading 60-nm gold particles on a cover glass was photographed on the same day as the single-molecule measurement and was used as a reference point for alignment between two channels. In order to keep the intensity per molecule of a fluorescent dye constant between images, the brightness and contrast were set to constant values (minimum: 0, maximum: 1800), and stack images were then converted to avi (8 bit) uncompressedly. Single molecule tracking (SMT) analysis was performed using G-count software (G-angstrom) formed based on a two-dimensional Gaussian fitting method. The VB-HMM analysis was performed using a program formed on LabView according to algorithm reported in the past[8,9,24].

Extraction of various parameters, curve fitting, and drawing were carried out from the results of SMT and VB-HMM analysis using Igor Pro 6 (WaveMetrix) as follows. The MSD of each track in the time interval not was calculated by the following expression[25].

[Math 1]

$$MSD(n\Delta t) = \frac{1}{N-1-n} \sum_{j=1}^{N-1-n} [\{x(j\Delta t + n\Delta t) - x(j\Delta t)\}^2 + \{y(j\Delta t + n\Delta t) - y(j\Delta t)\}^2] \quad (1)$$

Herein, n denotes the frame length; Δt denotes the frame rate (30.5 ms), and N denotes the total frame length of the track. $D_{Av}$ was calculated based on a two-dimensional diffusion equation by the following expression.

[Math 2]

$$D_{Av}(n\Delta t) = \frac{1}{M} \sum_{j=1}^{M} \frac{MSD_j(n\Delta t)}{4n\Delta t} \quad (2)$$

Herein, $MSD_j$ indicates the MSD of the $j^{th}$ track; and M indicates the total number of tracks. In this Example, $D_{Av}$ was calculated from the value of n=6 (nΔt=183 ms) allowing highly accurate detection of a stimulation-dependent change. The $EC_{50}$ and $IC_{50}$ of the ligand concentration-dependent change of $D_{Av}$ were calculated through fitting by Expressions 3 and 4, respectively.

[Math 3]

$$f(x) = bottom + \frac{top - bottom}{1 + \frac{EC_{50}}{x}}, \quad (3)$$

$$f(x) = top + \frac{bottom - top}{1 + \frac{IC_{50}}{x}}. \quad (4)$$

The MSD-Δt plot was fitted by Expression 5[26].

[Math 4]

$$MSD(\Delta t) = \frac{L^3}{3}\left(1 - \exp\left(\frac{-12D\Delta t}{L^2}\right)\right) \quad (5)$$

L denotes the diffusion limiting distance; and D denotes the diffusion coefficient calculated in an asymptote of Δt to 0.

Displacement at Δt (30.5 ms):

$r = \sqrt{MSD}$ [Math 5]

The histogram thereof was fitted by Expression 6 for each diffusion state[27].

[Math 6]

$$P(r) = \frac{r}{2D\Delta t}\exp\left(\frac{-r^2}{4D\Delta t}\right). \quad (6)$$

The histogram of the intensity distribution was fitted by Expression 7 based on the sum of N Gaussian functions.

[Math 7]

$$P(x) = \sum_{n=1}^{N} A_n \exp\left(-\frac{(x-nI)^2}{2n\sigma^2}\right) \quad (7)$$

Herein, n indicates the multimer size; and I and σ indicate the mean and standard deviation (SD), respectively, of the intensity distribution of one fluorescent dye molecule. N was determined using Akaike's information criterion. The I the σ of a TMR molecule were estimated to be 530 and 210, respectively, from measurement of a TMR-labeled CD86 molecule.

Colocalization of TMR-labeled mGluR3 and GFP-labeled CLC was defined as a track in which each bright spot was within 100 nm in the same frame. The positional accuracy of the bright spot tracking of TMR-labeled mGluR3 and GFP-labeled CLC was estimated to be 28 nm and 31 nm, respectively, from measurement of fixed samples. These values correspond to 1 SD of the displacement when fixed molecules were tracked. After image processing, the error between the positions of the same gold particle in two channels was estimated to be 18 nm. Accordingly, 100 nm corresponds to about 2 SD of the positional accuracy considering the total error. The time constant of colocalization was calculated by fitting the cumulative frequency distribution (FIG. 9(f)) by Expression 8.

[Math 8]

$$P(t) = A_1 \exp\left(-\frac{t}{\tau_1}\right) + A_2 \exp\left(-\frac{t}{\tau_2}\right) \quad (8)$$

The proportion of each component was calculated from the proportions of $A_1$ and $A_2$.

3-5. Preparation of Membrane Sample for In Vitro Biochemical Analysis

A membrane sample expressing mGluR3 for In vitro biochemical analysis was prepared by the following method[28]. HEK293 cells cultured to about 40% confluence in a 100-mm dish were transfected with mGluR3 pDNA and an empty pCAG vector as a mock each at 10 μg/dish by a calcium phosphate method. After the transfection, the cells were cultured in DMEM/F12 medium containing 10% FBS for 48 hours and were then collected, followed by centrifugation. The precipitation was washed with 1 mL of PBS (pH 7.4). Centrifugation was further performed. The precipitation was placed in a 1.5-mL tube and was homogenized with a pellet mixer in buffer A (50 mM HEPES (pH 6.5), 140 mM NaCl) in which 50% sucrose was dissolved, followed by centrifugation to separate supernatant and precipitate. The supernatant containing a large amount of plasma membrane fraction was diluted with double amount of buffer A, followed by centrifugation again. The precipitate containing the plasma membrane fraction was washed with buffer A and was stored at −80° C.

3-6. Western Blotting

A membrane fraction containing mGluR3 was solubilized with an SDS sample buffer (62.5 mM Tris-HCl (pH 6.8), 4% SDS, 10% glycerol, 0 or 2.5% β-mercaptoethanol) and was subjected to 5.5% SDS-PAGE. Proteins were transferred from the gel after the electrophoresis to a PVDF membrane and were subjected to labeling with an Rho1D4 antibody (primary antibody) and HRP-conjugated anti-mouse IgG (secondary antibody, Cell Signaling #7076). The protein labeled with the antibodies was treated with a luminescent reagent Amersham ECL prime Western blotting detection reagent (GE), and the luminescence was detected with ImageQuant LAS 500 (GE).

3-7. [³H]-Ligand Binding Experiment of mGluR3

A cell membrane fraction containing mGluR3 was resuspended in HBSS (containing 15 mM HEPES (pH 7.1) and not containing $NaHCO_3$, Sigma) having the same composition as that used in the single-molecule measurement, and the binding of [³H]-LY341495 to the membrane was measured at room temperature. A certain volume of the membrane fraction (1/32 volume of the membrane prepared from confluent HEK293 cells in a 100-mm dish) was mixed with a solution of [³H]-LY341495 diluted with HBSS to a final concentration of 0 to 1 μM (mixed solution volume: 20 μL), and the mixture was left to stand at room temperature for 30 minutes. Subsequently, the mixture containing [³H]-LY341495 was passed through a nitrocellulose membrane (0.45 μm HATF, Millipore) with a dot-blot apparatus (FLE396AA, ADVANTEC) to separate the membrane fraction and the solution. The nitrocellulose membrane to which the membrane fraction was bound was washed with HBSS (200 μL) twice and was dried for 1 hour. Each dot was excised from the nitrocellulose membrane and was placed in a cocktail for a liquid scintillation counter (Ultima Gold, PerkinElmer Life Sciences, Inc.), and the binding amount of [³H]-LY341495 was quantified with LS6500 (Beckman Coulter). The non-specific binding amount of [³H]-LY341495 was estimated by performing mock transfection and binding it to a HEK293 membrane fraction similarly prepared. $K_d$ was calculated from fitting result by an expression obtained by replacing the $EC_{50}$ in Expression 3 mentioned above with $k_d$. The competitive inhibition of binding of [³H]-LY341495 by LY379268 was also measured by the same method. The membrane fraction was mixed so as to give final concentrations of 100 nM [³H]-LY341495, 0-100 μM LY341495, and 0-1 μM MNI137 in HBSS. The mixture was left to stand at room temperature for 30 minutes, and the binding amount of [³H]-LY341495 was quantified by the same method as above. The $IC_{50}$ was calculated based on Expression 4.

3-8. [$^{35}$S]-GTPγS Binding Experiment

The G protein activation ability of mGluR3 was quantified by a modification of the method described in a past document[29]. A membrane fraction containing mGluR3 (final concentration: 11 nM) was solubilized with buffer B (50 mM HEPES (pH 6.5), 140 mM NaCl, and 3 mM $MgCl_2$) containing 0.02% n-dodecyl-β-D-maltopyranoside (DM; Dojindo) and was mixed with a ligand in various concentrations and Go protein purified from porcine brain. Each mixture was left to stand at 20° C. for 30 minutes. [$^{35}$S]-GTPγS was added to the mixture to start GDP/GTPγS exchange reaction. The composition except the ligand of the final mixture solution (20 μL) was 50 mM HEPES (pH 6.5), 140 mM NaCl, 5 mM $MgCl_2$, 0.01% DM, 0.03% sodium cholate, 5 nM [$^{35}$S]-GTPγS, 500 nM GTPγS (cold), and 500 nM GDP. A reaction stop solution (200 μL, 20 mM Tris/Cl (pH 7.4), 100 mM NaCl, 25 mM $MgCl_2$, 500 nM GTPγS (cold), and 500 nM GDP) was added to the mixture solution at 30 seconds after the addition of [$^{35}$S]-GTPγS to stop the incorporation of [$^{35}$S]-GTPγS into G protein, and immediately all the reaction solution was passed through a nitrocellulose membrane with the dot-blot apparatus to separate [$^{35}$S]-GTPγS bound to G protein. Subsequently, the nitrocellulose membrane was washed with buffer C (200 μL, 20 mM Tris/Cl (pH 7.4), 100 mM NaCl, and 25 mM $MgCl_2$) three times and was dried for 1 hour. Each dot was excised from the nitrocellulose membrane and was placed in a cocktail for a liquid scintillation counter (Ultima Gold, PerkinElmer Life Sciences, Inc.), and the binding amount of [$^{35}$S]-GTPγS was quantified with LS6500 (Beckman Coulter). The non-specific binding amount was estimated by performing mock transfection and binding it to a HEK293 membrane fraction similarly prepared. $EC_{50}$ and $IC_{50}$ were calculated using Expressions 3 and 4, respectively.

3-9. Saturation Binding Experiment of HaloTag TMR Ligand

HaloTag-fused or non-fused mGluR3 pDNA (1 μg/60-mm dish) was transfected into HEK293 cells grown to a confluence of about 70% by the lipofection method described above. After culturing overnight, the medium was replaced with DMEM (not containing phenol red and FBS) containing 0-2 μM HaloTag TMR ligand, followed by being left to stand at 37° C. in an environment containing 5% $CO_2$ for 30 minutes. After TMR staining, the 60-mm dish was washed with 3 mL of HBSS three times. The cells were suspended in buffer C (500 μL, 10 mM HEPES (pH 7.5), 140 mM NaCl, 4 mM KOH, 1 mM $MgCl_2$, and 1.5 mM $CaCl_2$) and were collected in a 1.5-mL tube. After centrifugation, the cellular precipitate was solubilized with 200 μL of buffer C containing 1% Triton X. After centrifugation again, the supernatant was collected, and the concentration of TMR bound to the solubilized receptor was quantified with a fluorescence spectrophotometer (RF-5300PC, Shimadzu). The sample was excited at 540 nm. The scattered light of the excitation light was removed with an 057 cut-off filter, and the fluorescence spectrum was then measured. As a standard sample, the TMR ligand in a known concentration was used (FIG. 2(a, b)). The non-specific binding was estimated by using a membrane fraction expressing mGluR3 not fused with HaloTag (FIG. 2(c)). The specific binding to HaloTag-fused mGluR3 was calculated by subtracting non-specific binding from the total binding amount to the cells expressing HaloTag-fused mGluR3. The specific binding and the non-specific binding were fitted using the following Hill equation (n: Hill coefficient).

[Math 9]

$$f(x) = \text{bottom} + \frac{\text{top} - \text{bottom}}{\left(1 + \frac{EC_{50}}{x}\right)^n} \quad (9)$$

REFERENCE DOCUMENTS

1. Tang, X. L., Wang, Y., Li, D. L., Luo, J. & Liu, M. Y. Orphan G protein-coupled receptors (GPCRs): biological functions and potential drug targets. Acta Pharmacol Sin 33, 363-71 (2012).
2. Santos, R. et al. A comprehensive map of molecular drug targets. Nat Rev Drug Discov 16, 19-34 (2017).
3. Zhang, R. & Xie, X. Tools for GPCR drug discovery. Acta Pharmacol Sin 33, 372-84 (2012).
4. Hemstapat, K. et al. A novel family of potent negative allosteric modulators of group II metabotropic glutamate receptors. J Pharmacol Exp Ther 322, 254-64 (2007).
5. DiRaddo, J. O. et al. Chloride is an Agonist of Group II and III Metabotropic Glutamate Receptors. Mol Pharmacol 88, 450-9 (2015).
6. Tora, A. S. et al. Allosteric modulation of metabotropic glutamate receptors by chloride ions. FASEB J 29, 4174-88 (2015).
7. Neubig, R. R. et al. International Union of Pharmacology Committee on Receptor Nomenclature and Drug Classification. XXXVIII. Update on terms and symbols in quantitative pharmacology. Pharmacol Rev 55, 597-606 (2003).
8. Persson, F., Linden, M., Unoson, C. & Elf, J. Extracting intracellular diffusive states and transition rates from single-molecule tracking data. Nat Methods 10, 265-9 (2013).
9. Okamoto, K. & Sako, Y. Variational Bayes analysis of a photon-based hidden Markov model for single-molecule FRET trajectories. Biophys J 103, 1315-24 (2012).
10. Calebiro, D. et al. Single-molecule analysis of fluorescently labeled G protein-coupled receptors reveals complexes with distinct dynamics and organization. Proc Natl Acad Sci USA 110, 743-8 (2013).
11. Mangmool, S. & Kurose, H. G(i/o) protein-dependent and -independent actions of Pertussis Toxin (PTX). Toxins (Basel) 3, 884-99 (2011).
12. Nobles, M., Benians, A. & Tinker, A. Heterotrimeric G proteins precouple with G protein-coupled receptors in living cells. Proc Natl Acad Sci USA 102, 18706-11 (2005).
13. Gales, C. et al. Probing the activation-promoted structural rearrangements in preassembled receptor-G protein complexes. Nat Struct Mol Biol 13, 778-86 (2006).
14. Qin, K., Dong, C., Wu, G. & Lambert, N. A. Inactive-state preassembly of G(q)-coupled receptors and G(q) heterotrimers. Nat Chem Biol 7, 740-7 (2011).
15. Kusumi, A. & Sako, Y. Cell surface organization by the membrane skeleton. Curr Opin Cell Biol 8, 566-74 (1996).
16. Hem, J. A. et al. Formation and dissociation of M1 muscarinic receptor dimers seen by total internal reflection fluorescence imaging of single molecules. Proc Natl Acad Sci USA 107, 2693-8 (2010).
17. De Lean, A., Stadel, J. M. & Lefkowitz, R. J. A ternary complex model explains the agonist-specific binding properties of the adenylate cyclase-coupled beta-adrenergic receptor. J Biol Chem 255, 7108-17 (1980).
18. Drake, M. T., Shenoy, S. K. & Lefkowitz, R. J. Trafficking of G protein-coupled receptors. Circ Res 99, 570-82 (2006).
19. Puthenveedu, M. A. & von Zastrow, M. Cargo regulates clathrin-coated pit dynamics Cell 127, 113-24 (2006).
20. Henry, A. G. et al. Regulation of endocytic clathrin dynamics by cargo ubiquitination. Dev Cell 23, 519-32 (2012).
21. Niwa, H., Yamamura, K. & Miyazaki, J. Efficient selection for high-expression transfectants with a novel eukaryotic vector. Gene 108, 193-9 (1991).
22. Gaidarov, I., Santini, F., Warren, R. A. & Keen, J. H. Spatial control of coated-pit dynamics in living cells. Nat Cell Biol 1, 1-7 (1999).
23. Tanaka, K. A. K. et al. Membrane molecules mobile even after chemical fixation. Nature Methods 7, 865-866 (2010).
24. Bronson, J. E., Fei, J., Hofman, J. M., Gonzalez, R. L., Jr. & Wiggins, C. H. Learning rates and states from biophysical time series: a Bayesian approach to model selection and single-molecule FRET data. Biophys J 97, 3196-205 (2009).
25. Kusumi, A., Sako, Y. & Yamamoto, M. Confined lateral diffusion of membrane receptors as studied by single particle tracking (nanovid microscopy). Effects of calcium-induced differentiation in cultured epithelial cells. Biophys J 65, 2021-40 (1993).
26. Xiao, Z. et al. Single-molecule study of lateral mobility of epidermal growth factor receptor 2/HER2 on activation. J Phys Chem B 112, 4140-5 (2008).
27. Wilson, K. M., Morrison, I. E., Smith, P. R., Fernandez, N. & Cherry, R. J. Single particle tracking of cell-surface HLA-DR molecules using R-phycoerythrin labeled monoclonal antibodies and fluorescence digital imaging. J Cell Sci 109 (Pt 8), 2101-9 (1996).
28. Yanagawa, M., Yamashita, T. & Shichida, Y. Glutamate acts as a partial inverse agonist to metabotropic glutamate receptor with a single amino acid mutation in the transmembrane domain. J Biol Chem 288, 9593-601 (2013).
29. Yanagawa, M., Yamashita, T. & Shichida, Y. Activation Switch in the Transmembrane Domain of Metabotropic Glutamate Receptor. Molecular Pharmacology 76, 201-207 (2009).
30. Fredriksson, R., Lagerstrom, M. C., Lundin, L. G. & Schioth, H. B. The G-protein-coupled receptors in the human genome form five main families Phylogenetic analysis, paralogon groups, and fingerprints. Mol Pharmacol 63, 1256-72 (2003).
31. Munk, C. et al. GPCRdb: the G protein-coupled receptor database-an introduction. Br J Pharmacol 173, 2195-207 (2016).

All publications, patents and patent applications cited in the present description are incorporated herein by reference in their entirety.

What is claimed is:

1. A method for evaluating activity of a G protein-coupled receptor (GPCR) comprising:

bringing a target substance into contact with a cell expressing a GPCR on a cell membrane, wherein the GPCR is labelled on a C-terminus with a fluorescent label; and using the fluorescent label attached to the GPCR as an index to determine diffusive dynamics of the GPCR on the cell membrane, as a mean square displacement, or as an average diffusion coefficient, wherein slow diffusive dynamics compared to that of a negative control indicates that the target substance is a GPCR agonist, or fast diffusive dynamics compared to that of the negative control indicates that the target substance is a GPCR inverse agonist, and wherein the negative control is the cell not brought into contact with the target substance, or the cell brought into contact with the vehicle.

* * * * *